United States Patent
Vazquez et al.

(10) Patent No.: US 11,286,281 B2
(45) Date of Patent: Mar. 29, 2022

(54) HOMODETIC CYCLIC PEPTIDES TARGETING ALPHA-4-BETA-7 INTEGRIN

(71) Applicant: Zealand Pharma A/S, Søborg (DK)

(72) Inventors: Manuel Perez Vazquez, Milton (CA); M. Monzur Morshed, Mississauga (CA); Adam Paul Kafal, Toronto (CA); Jennifer L. Hickey, Toronto (CA); Andrew Roughton, Port Hope (CA)

(73) Assignee: Zealand Pharma A/S, Søborg (DK)

( * ) Notice: Subject to any disclaimer, the term of this patent is extended or adjusted under 35 U.S.C. 154(b) by 73 days.

(21) Appl. No.: 16/611,518

(22) PCT Filed: May 10, 2018

(86) PCT No.: PCT/CA2018/000087
§ 371 (c)(1),
(2) Date: Nov. 7, 2019

(87) PCT Pub. No.: WO2018/205008
PCT Pub. Date: Nov. 15, 2018

(65) Prior Publication Data
US 2020/0095285 A1  Mar. 26, 2020

Related U.S. Application Data

(60) Provisional application No. 62/504,309, filed on May 10, 2017.

(51) Int. Cl.
*A61P 37/06* (2006.01)
*A61P 29/00* (2006.01)
*C07K 7/56* (2006.01)
*A61K 38/00* (2006.01)
*C07K 7/64* (2006.01)

(52) U.S. Cl.
CPC ............... *C07K 7/64* (2013.01); *A61P 29/00* (2018.01); *A61P 37/06* (2018.01); *C07K 7/56* (2013.01); *A61K 38/00* (2013.01)

(58) Field of Classification Search
CPC .......... A61K 38/00; A61P 29/00; A61P 37/06; C07K 7/56; C07K 7/64; Y02A 50/30
See application file for complete search history.

(56) References Cited

U.S. PATENT DOCUMENTS 5,296,604 A   3/1994  Hanko et al.
5,693,325 A   12/1997 Kahn
(Continued)

FOREIGN PATENT DOCUMENTS

CA   2427046 A1   11/2003
DE   3219113 A1   11/1983
(Continued)

OTHER PUBLICATIONS

Boer et al., Design and Synthesis of Potent and Selective α4β7 Integrin Antagonists, J. Med. Chem., vol. 44:2586-2592 (Jul. 26, 2001) (Year: 2001).*

(Continued)

*Primary Examiner* — Randall L Beane
(74) *Attorney, Agent, or Firm* — Clark & Elbing LLP

(57) ABSTRACT

There is described herein antagonists of α4β7 integrin, and more particularly cyclic peptide antagonists, such as compounds of formula (I).

18 Claims, 9 Drawing Sheets

Compound 17

Compound 16

(56) References Cited

U.S. PATENT DOCUMENTS

| | | | |
|---|---|---|---|
| 5,693,612 | A | 12/1997 | Jonczyk et al. |
| 5,693,750 | A | 12/1997 | Ohki et al. |
| 5,696,084 | A | 12/1997 | Lartey et al. |
| 5,705,481 | A | 1/1998 | Jonczyk et al. |
| 5,731,286 | A | 3/1998 | Harbeson et al. |
| 6,034,056 | A | 3/2000 | Dutta |
| 6,492,553 | B1 | 12/2002 | Hulme et al. |
| 9,533,985 | B2 | 1/2017 | Ueno et al. |
| 10,981,921 | B2* | 4/2021 | Vazquez ............. A61P 3/10 |
| 2008/0200398 | A1 | 8/2008 | Smyth et al. |
| 2011/0251247 | A1 | 10/2011 | Chubb et al. |
| 2014/0193465 | A1 | 7/2014 | Bhandari et al. |
| 2016/0159862 | A1 | 6/2016 | Bhandari et al. |
| 2019/0077805 | A1 | 3/2019 | Vazquez et al. |
| 2020/0165300 | A1* | 5/2020 | Vazquez ............. A61P 25/24 |

FOREIGN PATENT DOCUMENTS

| | | |
|---|---|---|
| JP | H10-508315 A | 8/1998 |
| WO | WO-96/00581 A1 | 1/1996 |
| WO | WO-96/20216 A1 | 7/1996 |
| WO | WO-97/03094 A1 | 1/1997 |
| WO | WO-2001/010799 A1 | 2/2001 |
| WO | WO-02/066500 A2 | 8/2002 |
| WO | WO-2008/046232 A1 | 4/2008 |
| WO | WO-2009/141687 A1 | 11/2009 |
| WO | WO-2010/105363 A1 | 9/2010 |
| WO | WO-2010/107832 A1 | 9/2010 |
| WO | WO-2014/059213 A1 | 4/2014 |
| WO | WO-2015/176035 A1 | 11/2015 |
| WO | WO-2016/054411 A1 | 4/2016 |
| WO | WO-2016/054445 A1 | 4/2016 |
| WO | WO-2017/079820 A1 | 5/2017 |
| WO | WO-2017/079821 A1 | 5/2017 |
| WO | WO-2018/085921 A1 | 5/2018 |

OTHER PUBLICATIONS

Boer et al., Design and Synthesis of Potent and Selective α4β7 Integrin Antagonists, J. Med. Chem., vol. 44:2586-2592 (2001) (Year: 2001).*

U.S. Appl. No. 16/985,096, Vazquez et al.

Extended European Search Report for European Application No. 16863253.7, dated Oct. 17, 2019 (6 pages).

Greene et al., "Preface to the Third Edition," *Protective Groups in Organic Synthesis*, Third Edition. John Wiley & Sons, Inc., v-vi (1999) (6 pages).

Supporting Information for Patil et al., "Second generation, arginine-rich (R-X'-R)(4)-type cellpenetrating alpha-omega-alpha-peptides with constrained, chiral omega-amino acids (X') for enhanced cargo delivery into cells," Bioorg Med Chem Lett. 24(17):4198-202 (2014).

Wagner et al., "New naturally occurring amino acids," Angew Chem Int Ed Engl. 22(11):816-28 (1983).

Quartara et al., "Influence of lipophilicity on the biological activity of cyclic pseudopeptide NK-2 receptor antagonist," J Med Chem. 37(21):3630-8 (1994).

Naveh et al., "Developing potent backbone cyclic peptides bearing the shared epitope sequence as rheumatoid arthritis drug-leads," Bioorg Med Chem Lett. 22(1):493-6 (2012).

Mohan et al., "Synthesis and biological activity of angiotensin II analogues containing a Val-His replacement, Val psi[CH(CONH2)NH]His," J Med Chem. 34(8):2402-10 (1991).

Treder et al., "Solid-phase synthesis of piperazinones via disrupted Ugi condensation," Org Lett. 16(17):4674-7 (2014).

International Search Report and Written Opinion Issued in Corresponding PCT Application No. PCT/CA2016/000274, dated Dec. 19, 2016.

Chen et al., "Synthesis of 12-membered macrocyclic templates and library analogs for PPI," Tetrahedron Letters 54:3298-301 (2013).

Pil et al., "Synthesis and electrophysiological characterization of cyclic morphiceptin analogues," Biochem Pharmacol. 67(10):1887-95 (2004).

Vercillo et al., "Design and synthesis of cyclic RGD pentapeptoids by consecutive Ugi reactions," Org Lett. 10(2):205-8 (2008).

Dörwald, F. Zaragoza. Side Reactions in Organic Synthesis: A Guide to Successful Synthesis Design, Weinheim: WILEY-VCH Verlag GmbH & Co. KGaA, 2005, Preface.

Suarez-Gea et al., "General Method for the Synthesis of Carbamoylmethyleneamino Pseudopeptides" Journal of Organic Chemistry, 59(13):3600-3603, 1994.

Couturier et al., "Aziridinium from N,N-dibenzyl serine methyl ester: synthesis of enantiomerically pure beta-amino and alpha,beta-diamino esters," Org Lett. 8(10):2183-6 (2006).

International Search Report and Written Opinion Issued in Corresponding PCT Application No. PCT/CA2017/000244, dated Feb. 8, 2018.

Tamamura et al., "Stereoselective synthesis of [L-Arg-L/D-3-(2-naphthyl)alanine]-type (E)-alkene dipeptide isosteres and its application to the synthesis and biological evaluation of pseudopeptide analogues of the CXCR4 antagonist FC131," J Med Chem. 48(2):380-91 (2005).

Hili et al., "Readily available unprotected amino aldehydes," J Am Chem Soc. 128(46):14772-3 (2006).

Rotstein et al., "Synthesis of peptide macrocycles using unprotected amino aldehydes," Nat Protoc. 5(11):1813-22 (2010).

Patil et al., "Second generation, arginine-rich (R-X'-R)(4)-type cell-penetrating a-ω-a-peptides with constrained, chiral ω-amino acids (X') for enhanced cargo delivery into cells," Bioorg Med Chem Lett. 24(17):4198-202 (2014).

Baktharaman et al., "Amino carbonyl compounds in organic synthesis", Aldrichimica Acta, 2008, 41 :109-117.

Burden et al., "Synthesis and biological activities of YkFA analogues: effects of position 4 substitutions and altered ring size on in vitro opioid activity," Bioorg Med Chem Lett. 12(2):213-6 (2002).

Hirose et al., "Total synthesis and determination of the absolute configuration of guadinomines B and C2," Chemistry 14(27):8220-38 (2008).

Verheijen et al., "An expeditious liquid-phase synthesis of cyclic peptide nucleic acids," Tetrahedron Letters 41:3991-5 (2000).

Yudin et al., "Overcoming the demons of protecting groups with amphoteric molecules," Chemistry 13(23):6538-42 (2007).

Dutta et al., "Potent cyclic monomeric and dimeric peptide inhibitors of VLA-4 (alpha4beta1 integrin)-mediated cell adhesion based on the Ile-Leu-Asp-Val tetrapeptide," J Pept Sci. 6(7):321-41 (2000).

Slama et al., "Convenient Synthesis of 1,2-Diamines from β-Chloro Amines: Precursors of New Substituted Piperazin-2-ones" Synthetic Communications, 43(17):2286-2293, 2013.

International Search Report and Written Opinion Issued in Corresponding PCT Application No. PCT/CA2016/000275, dated Feb. 28, 2017.

Hili et al., "Macrocyclization of linear peptides enabled by amphoteric molecules," J Am Chem Soc. 132(9):2889-91 (2010).

Murray et al., "The synthesis of cyclic tetrapeptoid analogues of the antiprotozoal natural product apicidin," Bioorg Med Chem Lett. 11(6):773-6 (2001).

Tal-Gan et al., "Backbone cyclic peptide inhibitors of protein kinase B (PKB/Akt)," J Med Chem. 54(14):5154-64 (2011).

Achmatowicz et al., The synthesis of L-proline derived hexaazamacrocyclic ligands of C3 symmetry via intramolecular methyl ester aminolysis, Tetrahedron: Asymmetry 12 (2001) 487-495.

International Search Report and Written Opinion Issued in PCT Application No. PCT/CA2018/000087, dated Aug. 7, 2018.

U.S. Appl. No. 62/421,117.

Partial Supplementary European Search Report for European Application No. 18798999.1, dated Feb. 2, 2021 (11 pages).

Gottschling et al., "Synthesis and NMR structure of peptidomimetic alpha-4-beta-7-integrin antagonists," Chembiochem. 3(6):575-8 (2002).

Examination Report for Indian Application No. 201817021544, dated May 18, 2020 (6 pages).

Partial Supplementary European Search Report for European Application No. 17870529.9, dated Apr. 23, 2020 (10 pages).

(56) References Cited

OTHER PUBLICATIONS

Extended European Search Report for European Application No. 17870529.9, dated Jul. 28, 2020 (14 pages).
Annex I: Summary of Product Characteristics for Entyvio, May 7, 2020 (93 pages).
Bova et al., "A label-free approach to identify inhibitors of alpha4beta7-mediated cell adhesion to MadCAM," J Biomol Screen. 16(5):536-44 (2011).
Berezov et al., "Medicine," Biological chemistry, Moscow, p. 34, 59 (1998).
Chen et al., "Vedolizumab for prevention of graft-versus-host disease after allogeneic hematopoietic stem cell transplantation," Blood Adv. 3(23):4136-4146 (Dec. 10, 2019).
Cushing et al., "Vedolizumab as a Novel Treatment for Refractory Collagenous Colitis: A Case Report," Am J Gastroenterol. 113(4):632-633 (Apr. 2018).
Dyson et al., Chemistry of synthetic medicines. *May's Chemistry of Synthetic Drugs, Fifth Edition.* Moscow: Mir. pp. 12-19 (1964).
Jennings et al., "Vedolizumab-Induced Remission in 3 Patients With Refractory Microscopic Colitis: A Tertiary Care Center Case Series," Inflamm Bowel Dis. 25(8):e97 (Jul. 17, 2019).
Kim et al., "Vedolizumab Treatment May Reduce Steroid Burden and Improve Histology in Patients With Eosinophilic Gastroenteritis," available in PMC Dec. 1, 2019, published in final edited form as: Clin Gastroenterol Hepatol. 16(12):1992-1994, Epub Mar. 27, 2018 (Dec. 2018) (7 pages).
Ribaldone et al., "Vedolizumab for treatment of chronic refractory pouchitis: a systematic review with pool analysis," Rev Esp Enferm Dig. 112(1):59-63 (Jan. 2020).
Wyant et al., "Development and validation of receptor occupancy pharmacodynamic assays used in the clinical development of the monoclonal antibody vedolizumab," Cytometry B Clin Cytom. 90(2):168-76 (Mar. 2016).
Yoosuf et al., "Evolving Therapy for Celiac Disease," Front Pediatr. 7:193 (May 14, 2019) (18 pages).
Extended European Search Report for European Application No. 18798999.1, dated Jun. 1, 2021 (14 pages).

* cited by examiner

Compound 18

Compound 19

HOMODETIC CYCLIC PEPTIDES TARGETING ALPHA-4-BETA-7 INTEGRIN

RELATED APPLICATIONS

This application claims priority to U.S. Provisional Patent Application No. 62/504,309 filed on May 10, 2017, the entirety of which is incorporated herein by reference.

FIELD OF THE INVENTION

The invention relates to antagonists of α4β7 integrin, and more particularly to cyclic peptide antagonists.

BACKGROUND OF THE INVENTION

Integrins are transmembrane receptors that are the bridges for cell-cell and cell-extracellular matrix (ECM) interactions. When triggered, integrins trigger chemical pathways to the interior (signal transduction), such as the chemical composition and mechanical status of the ECM.

Integrins are obligate heterodimers, having two different chains: the α (alpha) and β (beta) subunits.

The α4β7 integrin is expressed on lymphocytes and is responsible for T-cell homing into gut-associated lymphoid tissues through its binding to mucosal addressin cell adhesion molecule (MAdCAM), which is present on high endothelial venules of mucosal lymphoid organs.

Inhibitors of specific integrin-ligand interactions have been shown effective as anti-inflammatory agents for the treatment of various autoimmune diseases. For example, monoclonal antibodies displaying high binding affinity for α4β7 have displayed therapeutic benefits for gastrointestinal auto-inflammatory/autoimmune diseases, such as Crohn's disease, and ulcerative colitis.

There is a need to develop improved α4β7 antagonists to prevent or treat inflammatory conditions and/or autoimmune diseases.

Certain methods of making cyclic peptides (nacellins) are described in Applicant's PCT Publication No. WO 2010/105363. Nacellin antagonists of α4β7 integrin are described in Applicant's PCT Patent Application No. PCT/CA2016/000274. Multimer Nacellin antagonists of α4β7 integrin are described in Applicant's U.S. Provisional Patent Application No. 62/421,117.

SUMMARY OF THE INVENTION

In an aspect, there is provided a compound of formula (I):

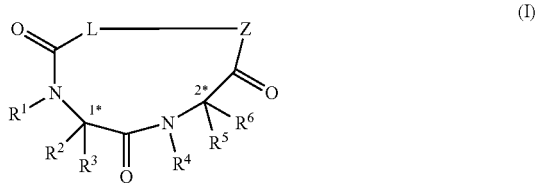

wherein $R^1$ is H; lower alkyl; aryl; heteroaryl; alkenyl; or heterocycle; all of which are optionally substituted at one or more substitutable positions with one or more suitable substituents;

$R^2$ and $R^3$ are each independently an amino acid chain of a proteinogenic or a non-proteinogenic alpha-amino acid, provided that $R^2$ and $R^3$ may be covalently linked to each other to form a ring or may be covalently linked to $R^1$ to form a cyclic secondary amine, $R^4$ is H, lower alkyl, benzyl, alkenyl, lower alkyloxy; aryl; heteroaryl; heterocycle; —C(O)R**, wherein R** is independently selected from alkyl, aryl, heteroaryl, amino, aminoalkyl, aminoaryl, aminoheteroaryl, alkoxy, aryloxy, heteroaryloxy; —CH₂C(O)R; or —C(O)Rc; all of which are optionally substituted at one or more substitutable positions with one or more suitable substituents, or along with $R^5$ or $R^6$, a cyclic side chain of a proteinogenic or a non-proteinogenic amino acid having, the N-terminus thereof being the N—R⁴, wherein the proteinogenic or a non-proteinogenic amino acid can be substituted with a suitable substituent;

$R^5$ and $R^6$ are independently selected from the amino acid side chains of a proteinogenic or a non-proteinogenic alpha-amino acid having the N-terminus thereof being the N—R⁴, or may form a cyclic side chain with $R^4$;

stereocentres 1* and 2* are each independently selected from R and S; and wherein Z is an amino terminus of an amino acid; —C=O— adjacent L is the carboxy terminus of an amino acid; and L along with Z and —C=O— is a peptide having the following formula:

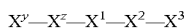

$$X^y—X^z—X^1—X^2—X^3$$

wherein $X^y$ is a proteinogenic or non-proteinogenic amino acid;

$X^z$ is absent or a proteinogenic or non-proteinogenic amino acid;

$X^1$ is Leucine or tert-butyl-Ala;

$X^2$ is Asp; and $X^3$ is Thr, Ile, MeThr, alloThr, Abu, Thr(OBn), Val, or alloIle.

In an aspect, there is provided a pharmaceutical composition comprising the compound or multimer described herein along with the pharmaceutically acceptable carrier.

In an aspect, there is provided a method of treating inflammation or an autoimmune disease in a patient, comprising administering to the patient a therapeutically effective amount of the compound or multimer described herein.

In an aspect, there is provided a method for treating a condition in a patient associated with a biological function of an α4β7 integrin, the method comprising administering to the patient a therapeutically effective amount of the compound or multimer described herein.

In an aspect, there is provided a method for treating a disease or condition in a patient comprising administering to the patient a therapeutically effective amount of the compound or multimer described herein, wherein the disease or condition is a local or systemic infection of a virus or retrovirus.

In an aspect, there is provided a method for treating a disease or condition in a patient comprising administering to the patient a therapeutically effective amount of the compound or multimer described herein, wherein the disease or condition is hepatitis A, B or C, hepatic encephalopathy, non-alcoholic steatohepatitis, cirrhosis, variceal bleeding, hemochromatosis, Wilson disease, tyrosinemia, alpha-1-antitrypsin deficiency, hepatocellular carcinoma, liver cancer, primary biliary cholangitis, primary biliary sclerosis, biliary tract disease, or autoimmune hepatitis In other aspects, there is provided the use of the compounds or multimers described herein for treating or preventing the diseases and conditions noted above.

In other aspects, there is provided the use of the compounds or multimers described herein in the preparation of a medicament for treating or preventing the diseases and conditions noted above.

In other aspects, there is provided compounds or multimers described herein for use in treating or preventing the diseases and conditions noted above.

BRIEF DESCRIPTION OF FIGURES

These and other features of the preferred embodiments of the invention will become more apparent in the following detailed description in which reference is made to the appended drawings and tables wherein.

DETAILED DESCRIPTION

Figure 1:
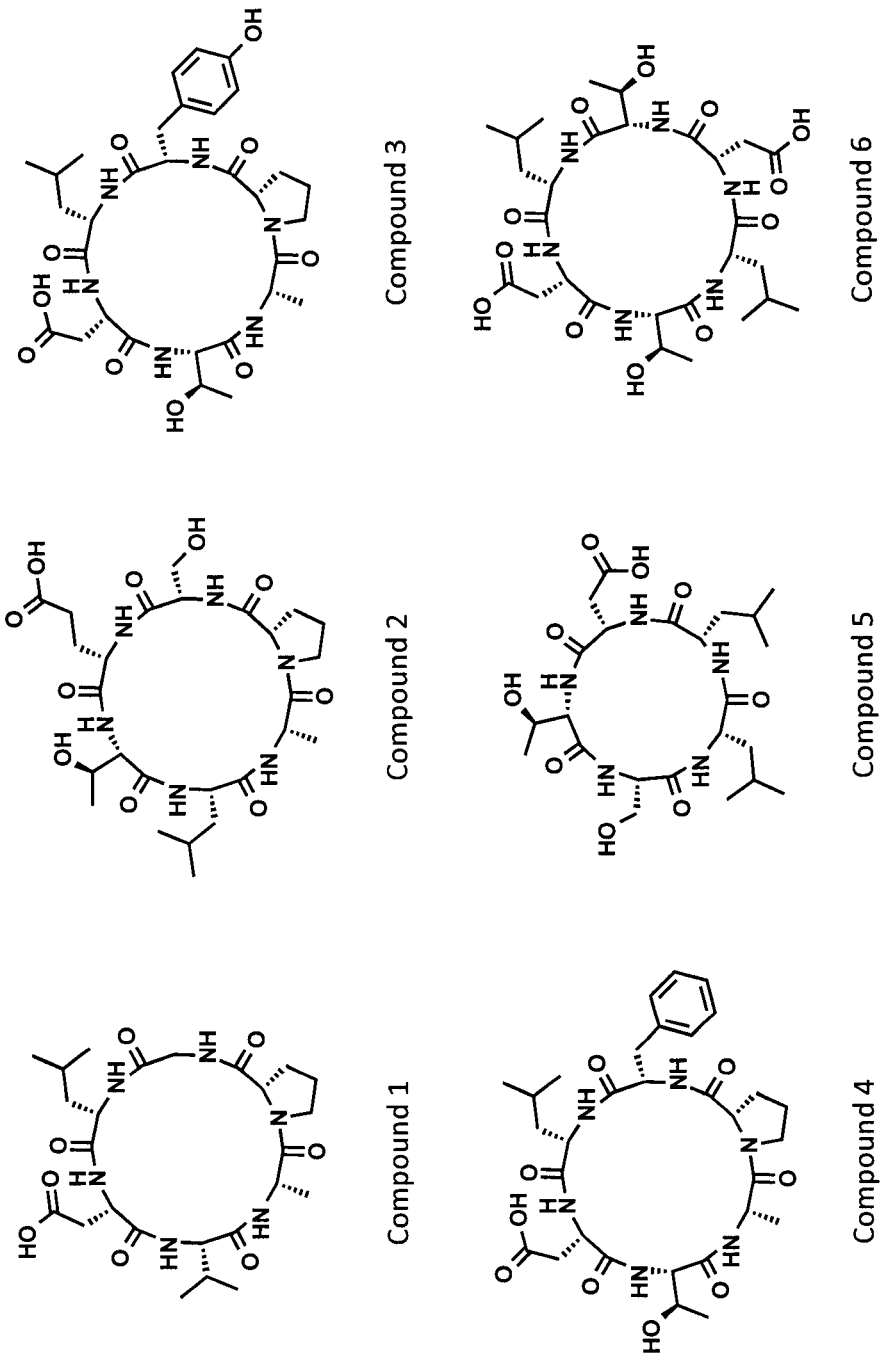
FIG. 1 shows representative compounds 1-6 of the present application.
Figure 2:
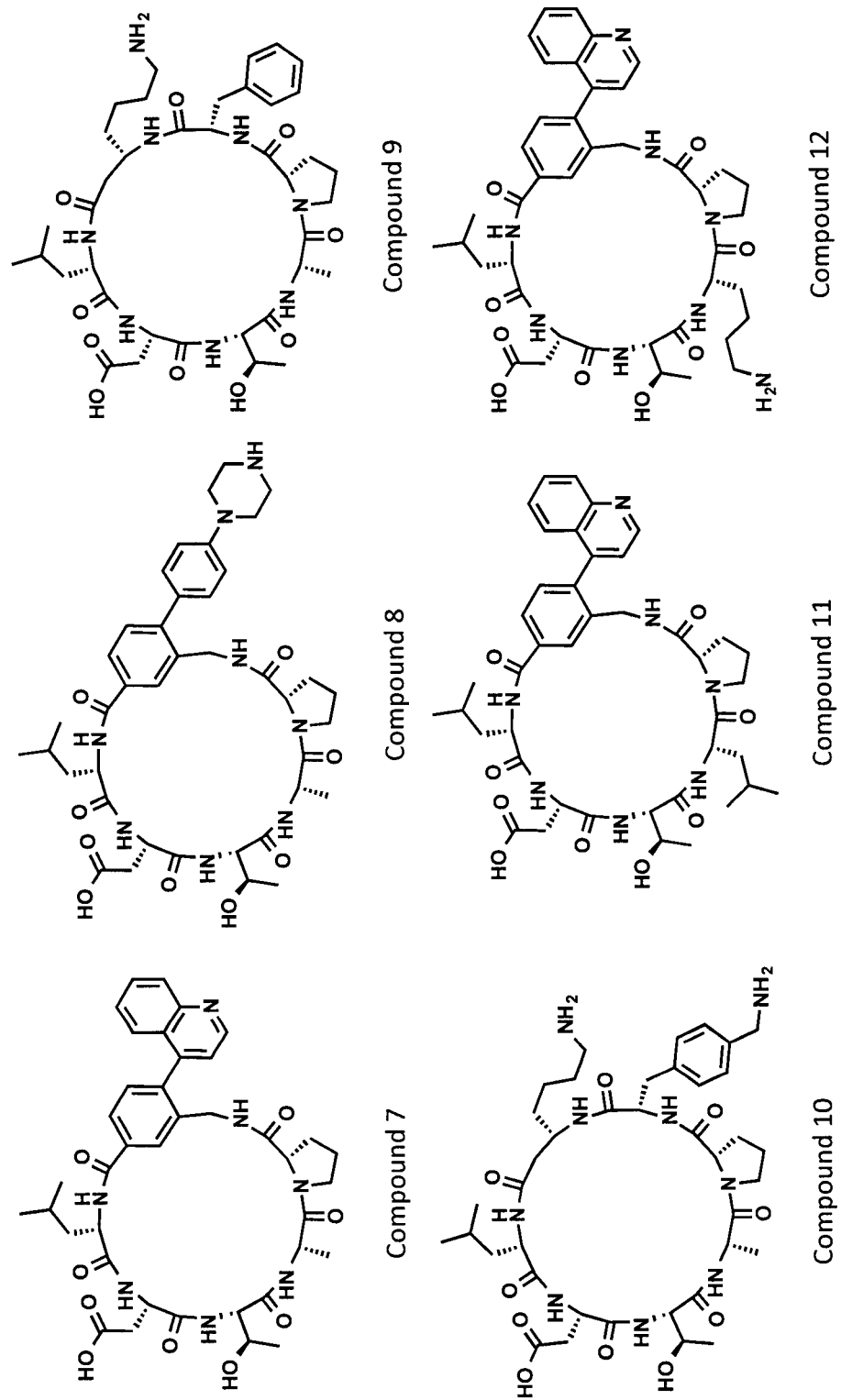
FIG. 2 shows representative compounds 7-12 of the present application.
Figure 3:
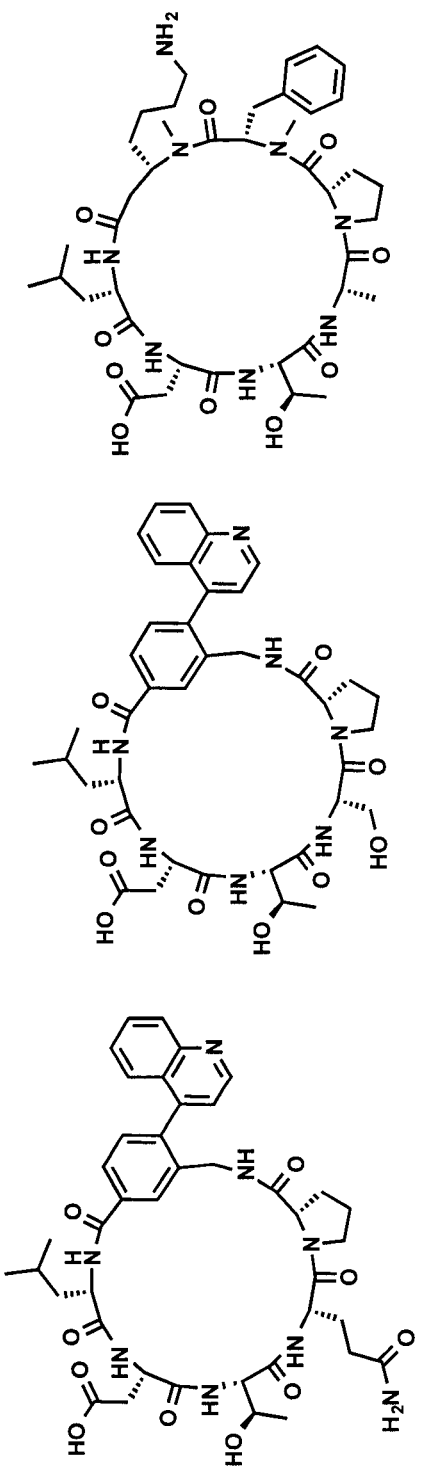
FIG. 3 shows representative compounds 13-15 of the present application.
Figure 4:
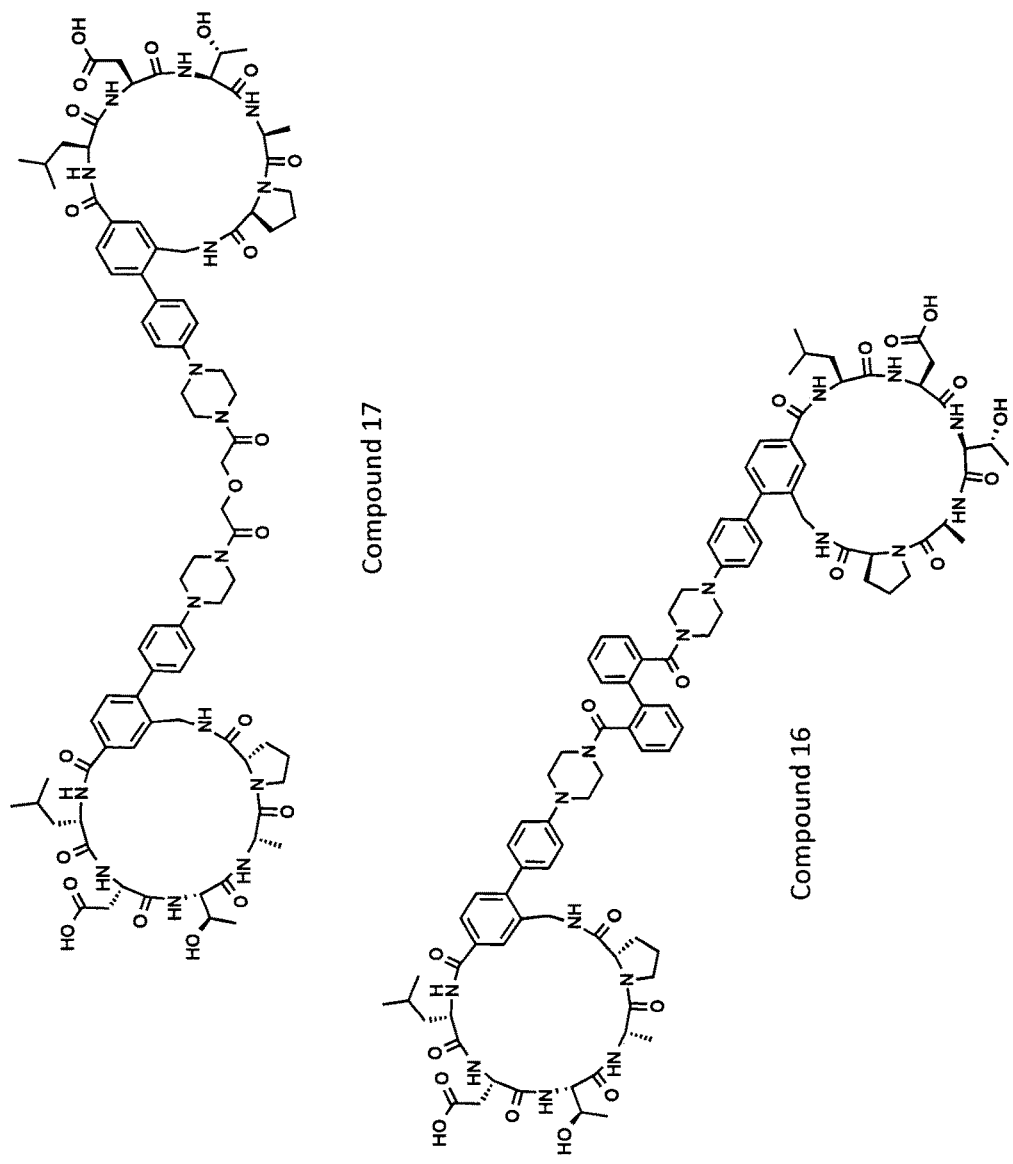
FIG. 4 shows representative multimer compounds 16-17 of the present application.
Figure 5:
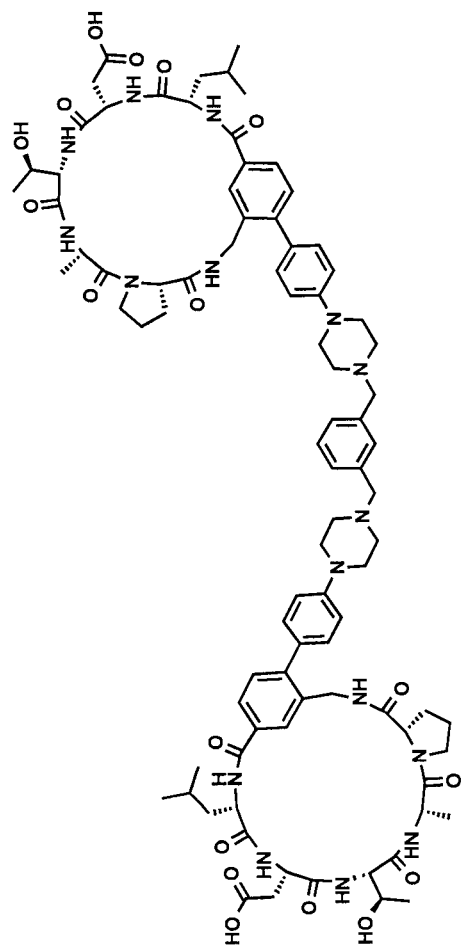
FIG. 5 shows representative multimer compounds 18-19 of the present application.
Figure 5:
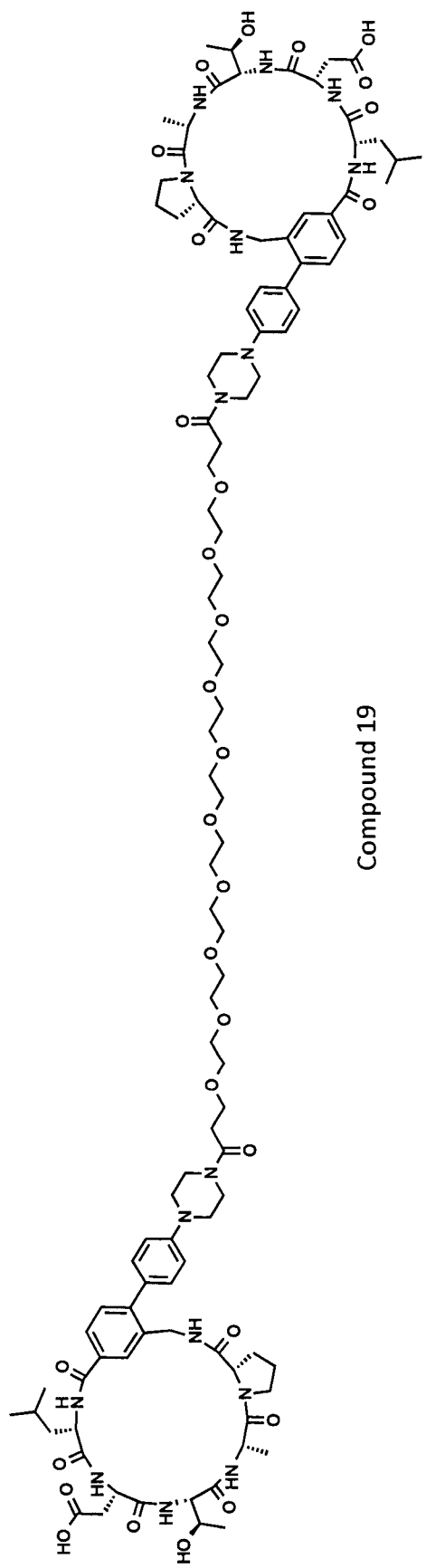

In the following description, numerous specific details are set forth to provide a thorough understanding of the invention. However, it is understood that the invention may be practiced without these specific details.

In an aspect, there is provided a compound of formula (I):

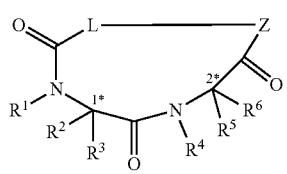

wherein
$R^1$ is H; lower alkyl; aryl; heteroaryl; alkenyl; or heterocycle; all of which are optionally substituted at one or more substitutable positions with one or more suitable substituents;

$R^2$ and $R^3$ are each independently an amino acid chain of a proteinogenic or a non-proteinogenic alpha-amino acid,
  provided that $R^2$ and $R^3$ may be covalently linked to each other to form a ring or may be covalently linked to $R^1$ to form a cyclic secondary amine, $R^4$ is H, lower alkyl, benzyl, alkenyl, lower alkyloxy; aryl; heteroaryl; heterocycle; —C(O)R**, wherein R** is independently selected from alkyl, aryl, heteroaryl, amino, aminoalkyl, aminoaryl, aminoheteroaryl, alkoxy, aryloxy, heteroaryloxy; —CH₂C(O)R; or —C(O)Rc; all of which are optionally substituted at one or more substitutable positions with one or more suitable substituents,
  or along with $R^5$ or $R^6$, a cyclic side chain of a proteinogenic or a non-proteinogenic amino acid having, the N-terminus thereof being the N—$R^4$, wherein the proteinogenic or a non-proteinogenic amino acid can be substituted with a suitable substituent;

$R^5$ and $R^6$ are independently selected from the amino acid side chains of a proteinogenic or a non-proteinogenic alpha-amino acid having the N-terminus thereof being the N—$R^4$, or may form a cyclic side chain with $R^4$;

stereocentres 1* and 2* are each independently selected from R and S; and wherein Z is an amino terminus of an amino acid; —C═O— adjacent L is the carboxy terminus of an amino acid; and L along with Z and —C═O— is a peptide having the following formula:

$$X^y\text{—}X^z\text{—}X^1\text{—}X^2\text{—}X^3$$

wherein $X^y$ is a proteinogenic or non-proteinogenic amino acid;
$X^z$ is absent or a proteinogenic or non-proteinogenic amino acid;
$X^1$ is Leucine or tert-butyl-Ala;
$X^2$ is Asp; and
$X^3$ is Thr, Ile, MeThr, alloThr, Abu, Thr(OBn), Val, or alloIle.

As used herein, the term "amino acid" refers to molecules containing an amine group, a carboxylic acid group and a side chain that varies. Amino acid is meant to include not only the twenty amino acids commonly found in proteins but also non-standard amino acids and unnatural amino acid derivatives known to those of skill in the art, and therefore includes, but is not limited to, alpha, beta and gamma amino acids. Peptides are polymers of at least two amino acids and may include standard, non-standard, and unnatural amino acids. A peptide is a polymer of two or more amino acids. The following abbreviations are used herein:

| Abbreviation | Description |
| --- | --- |
| 1,2-cis-ACHC | cis-2-aminocyclohexanecarboxylic acid |
| 1,2-trans-ACHC | trans-2-aminocyclohexanecarboxylic acid |

-continued

| Abbreviation | Description |
| --- | --- |
| 1Nal | 1-napthylalanine |
| 2Abz | anthranilic acid, 2-aminobenzoic acid |
| 2Igl | 2-indanylglycine |
| 2Nal | 2-napthylalanine |
| Abu | 2-aminobutyric acid |
| Aic | aminoindan-2-carboxylic acid |
| alloIle | allo-sioleucine, (2S,3R)-2-amino-3-methylpentanoic acid |
| alloThr | allo-threonine, (2S,3S)-2-amino-3-hydroxybutyric acid |
| alphaMePhe | α-methyl-phenylalanine, (S)-(−)-2-amino-2-methyl-3-phenylpropionic acid |
| Asp(ethyl ester) | aspartic acid β-ethyl ester |
| Atc | 2-aminotetraline-2-carboxylic acid |
| Aze | azetidine-2-carboxylic acid |
| BHT | butylated hydroxytoluene |
| Bip | biphenylalanine |
| C10 | sebacic acid |
| C12 | dodecanedioic |
| C7 | pimelic acid |
| C8 | suberic acid |
| C9 | azelaic acid |
| Cha | β-cyclohexyl alanine, (S)-2-amino-3-cyclohexylpropionic acid |
| Chg | cyclohexyl glycine |
| cis-dhyp | cis-D-4-Hydroxyproline, (2R,4R)-4-Hydroxypyrrolidine-2-carboxylic acid |
| cycloLeu | cyclo leucine, 1-Aminocyclopentane-1-carboxylic acid |
| cyclopropylAla | β-cyclopropyl alanine, (S)-2-amino-3-cyclopropyl-propionic acid |
| d2Igl | 2-indanyl-D-glycine |
| Dap(Cbz) | Nβ-Z-2,3-diaminopropionic acid |
| DBU | 1,8-diazabicyclo[5.4.0]undec-7-ene |
| DEPBT | 3-(diethoxyphosphoryloxy)-1,2,3-benzotriazin-4(3H)-one |
| dHyp | trans-D-4-hydroxyproline, (2R,4S)-4-hydroxypyrrolidine-2-carboxylic acid |
| DIAD | diisopropyl azodicarboxylate |
| DIG | diglycolic acid |
| DIPEA | N,N-diisopropylethylamine |
| DMAP | 4-(Dimethylamino)pyridine |
| dMeArg | N-methyl-D-arginine |
| dMebetaHomoLys | N-methyl-D-β-homoLys |
| dMeLys | N-methyl-D-Lysine |
| DMF | N,N-dimethylformamide |
| DMSO | dimethyl sulfoxide |
| dNle | D-norleucine |
| dOrn | D-ornithine |
| dOrn(dimethyl) | Nδ-dimethyl-D-ornithine |
| dPip | D-pipecolic acid, D-homoPro |
| dSer(OBn) | O-benzyl-D-serine |
| dTic | (3R)-1,2,3,4-tetrahydroisoquinoline-3-carboxylic acid |
| dTiq | D-1,2,3,4-tetrahydroisoquinoline-1-carboxylic acid |
| dTyr(OAllyl) | O-allyl-D-tyrosine |
| dTyr(OBn) | O-benzyl-D-tyrosine |
| EDC | N-(3-Dimethylaminopropyl)-N'-ethylcarbodiimide hydrochloride |
| Fmoc | 9-fluorenylmethoxycarbonyl |
| HATU | O-(7-azabenzotriazol-1-yl)-N,N,N',N'-tetramethyluronium hexafluorophosphate |
| HCTU | 2-(6-chloro-1H-benzotriazole-1-yl)-1,1,3,3-tetramethylaminium hexafluorophosphate |
| HFIP | 1,1,1,3,3,3-hexafluoro-2-propanol |
| His(Bn) | Nτ-benzyl-histidine |
| HomocycloLeu | homocyclo leucine, 1-Aminocyclohexanecarboxylic acid |
| Hyp | trans-4-hydroxyproline, (2S,4R)-4-hydroxypyrrolidine-2-carboxylic acid |
| Hyp(OBn) | O-benzyl-trans-4-hydroxyproline |
| MeAsp | N-methyl aspartic acid |
| MebetaHomoLys | N-methyl β-homoLysine |
| MebetaHomoLys(Me)2 | Nα-methyl-Nε-dimethyl-β-homoLysine |
| MeLeu | N-methyl leucine |
| MeMet | N-methyl methionine |
| MePhe | N-methyl phenylalanine |
| metaY(Opr) | metaTyrosine |
| MeThr | N-methyl threonine |
| MeTyr | N-methyl tyrosine |
| NMP | N-methylpyrrolidone |
| Nosyl chloride | 2-nitrobenzenesulfonyl chloride |
| Nva | norvaline |
| Orn(acetamide) | Nδ-acetamide-ornithine |
| Orn(benzamide) | Nδ-benzamide-ornithine |
| Orn(ethylcarbamate) | Nδ-ethylcarbamate-ornithine |
| Orn(methanesulfonamide) | Nδ-methanesulfonamide-ornithine |
| Orn(pentyl amide) | Nδ-pentyl amide-ornithine |
| PDA | 1,4-phenyldiacetic acid |
| Pen | penicillamine, β,β-dimethyl-cysteine |
| Pip | pipecolic acid, homoPro |

| Abbreviation | Description |
| --- | --- |
| Sar | sarcosine, N-methyl glycine |
| tertbutylAla | β-tert-butyl alanine, neopentylglycine |
| TFA | trifluoroacetic acid |
| TFE | 2,2,2-Trifluoroethanol |
| THF | tetrahydrofuran |
| Thr(OBn) | O-benzyl-threonine |
| Thr(OEt) | O-ethyl-threonine |
| Thr(OMe) | O-methyl-threonine |
| Tic | (3S)-1,2,3,4-tetrahydroisoquinoline-3-carboxylic acid |
| TIS | triisopropylsilane |
| Tyr(2-methoxy diaryl ether) | O-2-methoxy-phenyl-tyrosine |
| Tyr(2-tolyl diaryl ether) | O-2-methyl-phenyl-tyrosine |
| Tyr(3,4-difluoro diaryl ether) | O-3,4-difluoro-phenyl-tyrosine |
| Tyr(3,4-dimethyl diaryl ether) | O-3,4-dimethyl-phenyl-tyrosine |
| Tyr(3-CO2Me diaryl ether) | O-3-methylester-phenyl-tyrosine |
| Tyr(3-fluoro diaryl ether) | O-3-fluoro-phenyl-tyrosine |
| Tyr(3-methoxy diaryl ether) | O-3-methoxy-phenyl-tyrosine |
| Tyr(3-methyl diaryl ether) | O-3-methyl-phenyl-tyrosine |
| Tyr(4-CF3 diaryl ether) | O-4-trifluoromethyl-phenyl-tyrosine |
| Tyr(4-CO2H diaryl ether) | O-4-carboxylate-phenyl-tyrosine |
| Tyr(4-CO2Me diaryl ether) | O-4-methylester-phenyl-tyrosine |
| Tyr(4-fluoro diaryl ether) | O-4-fluoro-phenyl-tyrosine |
| Tyr(4-methoxy diaryl ether) | O-4-methoxy-phenyl-tyrosine |
| Tyr(OAllyl) | O-allyl-tyrosine |
| Tyr(OPh) | O-phenyl-tyrosine |
| vinyl-Br-Leu | 2-amino-4-bromo-4-pentenoic acid |

The term "suitable substituent" as used in the context of the present invention is meant to include independently H; hydroxyl; cyano; alkyl, such as lower alkyl, such as methyl, ethyl, propyl, n-butyl, t-butyl, hexyl and the like; alkoxy, such as lower alkoxy such as methoxy, ethoxy, and the like; aryloxy, such as phenoxy and the like; vinyl; alkenyl, such as hexenyl and the like; alkynyl; formyl; haloalkyl, such as lower haloalkyl which includes $CF_3$, $CCl_3$ and the like; halide; aryl, such as phenyl and napthyl; heteroaryl, such as thienyl and furanyl and the like; amide such as $C(O)NR_aR_b$, where $R_a$ and $R_b$ are independently selected from lower alkyl, aryl or benzyl, and the like; acyl, such as $C(O)-C_6H_5$, and the like; ester such as $-C(O)OCH_3$ and the like; ethers and thioethers, such as O-Bn and the like; thioalkoxy; phosphino; and $-NR_aR_b$, where $R_a$ and $R_b$ are independently selected from lower alkyl, aryl or benzyl, and the like. It is to be understood that a suitable substituent as used in the context of the present invention is meant to denote a substituent that does not interfere with the formation of the desired product by the processes of the present invention.

As used in the context of the present invention, the term "lower alkyl" as used herein either alone or in combination with another substituent means acyclic, straight or branched chain alkyl substituent containing from one to six carbons and includes for example, methyl, ethyl, 1-methylethyl, 1-methylpropyl, 2-methylpropyl, and the like. A similar use of the term is to be understood for "lower alkoxy", "lower thioalkyl", "lower alkenyl" and the like in respect of the number of carbon atoms. For example, "lower alkoxy" as used herein includes methoxy, ethoxy, t-butoxy.

The term "alkyl" encompasses lower alkyl, and also includes alkyl groups having more than six carbon atoms, such as, for example, acyclic, straight or branched chain alkyl substituents having seven to ten carbon atoms.

The term "aryl" as used herein, either alone or in combination with another substituent, means an aromatic mono- cyclic system or an aromatic polycyclic system. For example, the term "aryl" includes a phenyl or a napthyl ring, and may also include larger aromatic polycyclic systems, such as fluorescent (e.g. anthracene) or radioactive labels and their derivatives.

The term "heteroaryl" as used herein, either alone or in combination with another substituent means a 5, 6, or 7-membered unsaturated heterocycle containing from one to 4 heteroatoms selected from nitrogen, oxygen, and sulphur and which form an aromatic system. The term "heteroaryl" also includes a polycyclic aromatic system comprising a 5, 6, or 7-membered unsaturated heterocycle containing from one to 4 heteroatoms selected from nitrogen, oxygen, and sulphur.

The term "cycloalkyl" as used herein, either alone or in combination with another substituent, means a cycloalkyl substituent that includes for example, but is not limited to, cyclopropyl, cyclobutyl, cyclopentyl, cyclohexyl and cycloheptyl.

The term "cycloalkyl-alkyl-" as used herein means an alkyl radical to which a cycloalkyl radical is directly linked; and includes, but is not limited to, cyclopropylmethyl, cyclobutylmethyl, cyclopentylmethyl, 1-cyclopentylethyl, 2-cyclopentylethyl, cyclohexylmethyl, 1-cyclohexylethyl and 2-cyclohexylethyl. A similar use of the "alkyl" or "lower alkyl" terms is to be understood for aryl-alkyl-, aryl-lower-alkyl- (e.g. benzyl), -lower alkyl-alkenyl (e.g. allyl), heteroaryl-alkyl-, and the like as used herein. For example, the term "aryl-alkyl-" means an alkyl radical, to which an aryl is bonded. Examples of aryl-alkyl- include, but are not limited to, benzyl (phenylmethyl), 1-phenylethyl, 2-phenylethyl and phenylpropyl.

As used herein, the term "heterocycle", either alone or in combination with another radical, means a monovalent radical derived by removal of a hydrogen from a three- to seven-membered saturated or unsaturated (including aromatic) cyclic compound containing from one to four heteroatoms selected from nitrogen, oxygen and sulfur. Examples of such heterocycles include, but are not limited to, aziridine, epoxide, azetidine, pyrrolidine, tetrahydrofuran, thiazolidine, pyrrole, thiophene, hydantoin, diazepine, imidazole, isoxazole, thiazole, tetrazole, piperidine, piperazine, homopiperidine, homopiperazine, 1,4-dioxane, 4-morpholine, 4-thiomorpholine, pyridine, pyridine-N-oxide or pyrimidine, and the like.

The term "alkenyl", as used herein, either alone or in combination with another radical, is intended to mean an unsaturated, acyclic straight chain radical containing two or more carbon atoms, at least two of which are bonded to each other by a double bond. Examples of such radicals include, but are not limited to, ethenyl (vinyl), 1-propenyl, 2-propenyl, and 1-butenyl.

The term "alkynyl", as used herein is intended to mean an unsaturated, acyclic straight chain radical containing two or more carbon atoms, at least two of which are bonded to each other by a triple bond. Examples of such radicals include, but are not limited to, ethynyl, 1-propynyl, 2-propynyl, and 1-butynyl.

The term "alkoxy" as used herein, either alone or in combination with another radical, means the radical —O—($C_{1-n}$)alkyl wherein alkyl is as defined above containing 1 or more carbon atoms, and includes for example methoxy, ethoxy, propoxy, 1-methylethoxy, butoxy and 1,1-dimethylethoxy. Where n is 1 to 6, the term "lower alkoxy" applies, as noted above, whereas the term "alkoxy" encompasses "lower alkoxy" as well as alkoxy groups where n is greater than 6 (for example, n=7 to 10). The term "aryloxy" as used herein alone or in combination with another radical means —O-aryl, wherein aryl is defined as noted above.

A protecting group or protective group is a substituent introduced into a molecule to obtain chemoselectivity in a subsequent chemical reaction. Many protecting groups are known in the art and a skilled person would understand the kinds of protecting groups that would be incorporated and could be used in connection with the methods described herein. In "protecting group based peptide synthesis", typically solid phase peptide synthesis, the desired peptide is prepared by the step-wise addition of amino acid moieties to a building peptide chain. The two most widely used protocols, in solid-phase synthesis, employ tert-butyloxycarbonyl (Boc) or 9-fluorenylmethoxycarbonyl (Fmoc) as amino protecting groups. Amino protecting groups generally protect an amino group against undesirable reactions during synthetic procedures and which can later be removed to reveal the amine. Commonly used amino protecting groups are disclosed in Greene, T. W. et al., Protective Groups in Organic Synthesis, 3rd Edition, John Wiley & Sons (1999). Amino protecting groups include acyl groups such as formyl, acetyl, propionyl, pivaloyl, t-butylacetyl, 2-chloroacetyl, 2-bromoacetyl, trifluoroacetyl, trichloroacetyl, o-nitrophenoxyacetyl, alpha-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; alkoxy- or aryloxy-carbonyl groups (which form urethanes with the protected amine) such as benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, alpha-,alpha-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like. Amine protecting groups also include cyclic amino protecting groups such as phthaloyl and dithiosuccinimidyl, which incorporate the amino nitrogen into a heterocycle. Typically, amino protecting groups include formyl, acetyl, benzoyl, pivaloyl, t-butylacetyl, phenylsulfonyl, Alloc, Teoc, benzyl, Fmoc, Boc and Cbz. It is well within the skill of the ordinary artisan to select and use the appropriate amino protecting group for the synthetic task at hand.

In some embodiments, $R^1$ is H. In other embodiments, $R^2$ or $R^3$ is covalently linked to $R^1$ to form proline having $NR^1$ as the N-terminus.

In some embodiments, $R^2$ and $R^3$ are not both H.

In some embodiments, $R^2$ and $R^3$ are each independently selected from the group consisting of amino acid chains of a proteinogenic or a non-proteinogenic alpha-amino acids.

In some embodiments, $R^2$ and $R^3$ are H and $CH_3$ respectively or vice versa.

In some embodiments, $R^2$ or $R^3$ is —CH2-S—$R^s$, wherein $R^s$ is selected from lower alkyl; lower amino alkyl; aryl; heteroaryl; alkenyl; or heterocycle; all of which are optionally substituted at one or more substitutable positions with one or more suitable substituents; preferably $R^s$ is phenyl or phenyl substituted with lower alkyl, halogen; or lower amino alkyl.

In some embodiments, $R^4$ is H. In other embodiments, $R^4$ and either $R^5$ or $R^6$ form a ring resulting in a proline residue having N—$R^4$ as its N-terminus.

In some embodiments, n is 1.

In some embodiments, Z along with L and —C=O is as shown in any one of compounds 1-19.

In some embodiments, wherein $X^1$ is Leu.

In some embodiments, $X^2$ is Asp.

In some embodiments, $X^3$ is Thr.

In some embodiments, $X^3$ is Val.

In some embodiments, $X^3$ is Ile.

In some embodiments, $X^y$ and $X^z$ are each independently a proteinogenic or non-proteinogenic alpha-amino acid.

In some embodiments, $X^z$ is a proteinogenic or non-proteinogenic beta-amino acid.

In some embodiments, $X^y$ and $X^x$ are each a primary amino acid.

In some embodiments, $X^y$ is (1,2-cis-ACHC), (2,4-dichloro-MePhe), (2,4-dichloro-Phe), (2-aminomethyl-dPhe), (2-aminomethyl-Phe), (2-aza-Phe), (2-bromo-Phe), (2-CF3-Phe), (2-chloro-Phe), (2-fluoro-MePhe), (2-fluoro-Phe), (2-iodo-dPhe), (2-iodo-Phe), (2-phenyl-dPhe), (2-phenyl-Phe), (3,3-diphenyl-Ala), (3,4,5-trifluoro-Phe), (3,4-dimethoxy-Phe), (3,5-dibromo-Tyr), (3-aminomethyl-4-bromo-benzoic acid), (3-aminomethyl-4-morpholinyl-benzoic acid), (3-aminomethyl-4-piperidinyl-benzoic acid), (3-aminomethyl-5-bromo-benzoic acid), (3-aminomethyl-6-bromo-benzoic acid), (3-aminomethyl-benzoic acid), (3-aminomethyl-dPhe), (3-aminomethyl-Phe), (3-aza-dPhe), (3-aza-Phe), (3-benzothienyl-Ala), (3-benzothienyl-dAla), (3-iodo-Phe), (3-phenyl-dPhe), (3-phenyl-Phe), (4-amino-dPhe), (4-aminomethyl-dPhe), (4-aminomethyl- Phe), (4-aminomethyl-Phe)-reduced, (4-amino-Phe), (4-aza-dPhe), (4-aza-Phe), (4-guanidino-Phe), (4-iodo-Phe), (N-benzyl-3-aminomethyl-benzoic acid), (N-benzyl-Gly), (N-methyl-3-aminomethyl-benzoic acid), (piperidine-4-amino-4-carboxylic acid), (vinyl-Br-Leu), [(2-piperazinyl-2-Phenyl)-dPhe], [(2-piperazinyl-2-Phenyl)-Phe], [1-(S)-isoindoline-carboxylic acid], [2-(2,5-dimethyl-isoxazole)-dPhe], [2-(2,5-dimethyl-isoxazole)-Phe], [2-(2,6-dimethylphenyl)-Phe], [2-(2-bromo-3-Pyridyl)-Phe], [2-(2-chloro-6-methoxyphenyl)-Phe], [2-(2-methoxy-phenyl)-Phe], [2-(2-pyridyl)-4-thiazolyl-Ala], [2-(2-trifluoromethoxy-phenyl)-dPhe], [2-(3-bromo-2-Pyridyl)-Phe], [2-(3-methoxy-phenyl)-Phe], [2-(3-pyridyl)-4-thiazolyl-Ala], [2-(3-Pyridyl)-Phe], [2-(3-quinolinyl)-Phe], [2-(4-methoxy-phenyl)-Phe], [2-(4-pyridyl)-4-thiazolyl-Ala], [2-(4-Pyridyl)-Phe], [2-(4-quinolinyl)-Phe], [2-(5-quinolinyl)-dPhe], [2-(5-quinolinyl)-MePhe], [2-(5-quinolinyl)-Phe], [2-(5-quinolinyl)-Phe]-reduced, [2-(amino-benzyl)-4-thiazolyl-Ala], [2-(benzothiazol-5-yl)-Phe], [2-[2,5-Bis(trifluoromethyl)phenyl]-Phe], [2-[3-(1-piperazinyl) phenyl]-Phe]-betaHomoLys, [2-[4-(1-piperazinyl)phenyl]-Phe], [2-iodo-Phe], [3-(2,6-dimethoxy-phenyl)-dPhe], [3-(2,6-dimethoxy-phenyl)-Phe], [3-(2,6-dimethyl-phenyl)-Phe], [3-(2-aminobenzyl-4-thiazolyl)-Ala], [3-(2-chloro-6-methoxy-phenyl)-Phe], [3-(2-methoxy-phenyl)-dPhe], [3-(2-methoxy-phenyl)-Phe], [3-(2-thienyl)-dAla, [3-(2-trifluoromethoxy-phenyl)-dPhe], [3-(2-trifluoromethoxy-phenyl)-Phe], [3-(3,4-difluoro-phenyl)-Phe], [3-(3'-pyridyl)-Ala], [3-(4-Quinolinyl)-dPhe], [3-(4-thiazolyl)-Ala], [3-(4-thiazolyl)-Ala]-reduced, [3-(4-thiazolyl)-dAla], [3-(5-quinolinyl)-dPhe], [3-(benzothiazol-5-yl)-Phe], [3-(quinolin-4-yl)-Phe], [3-aminomethyl-(4-methylpyrazole-3-yl)-benzoic acid], [3-aminomethyl-4-(2,5-dimethoxy-phenyl)-benzoic acid], [3-aminomethyl-4-(2,5-dimethyl-isoxazole)-benzoic acid], [3-aminomethyl-4-(2-aminomethylphenyl)-benzoic acid], [3-aminomethyl-4-(2-fluoro-pyridyl)-benzoic acid], [3-aminomethyl-4-(3-aminomethylphenyl)-benzoic acid], [3-aminomethyl-4-(3-aza-phenyl)-benzoic acid], [3-aminomethyl-4-(3-CF3-phenyl)-benzoic acid], [3-aminomethyl-4-(3-N,N-dimethylaniline)-benzoic acid], [3-aminomethyl-4-(3-N,N-dimethyl-diaryl ether)-benzoic acid], [3-aminomethyl-4-(3-quinolinyl)-benzoic acid], [3-aminomethyl-4-(3-thiophenyl)-benzoic acid], [3-aminomethyl-4-(4-aminomethylphenyl)-benzoic acid], [3-aminomethyl-4-(4-aza-phenyl)-benzoic acid], [3-aminomethyl-4-(4-carboxy)-phenyl)-benzoic acid], [3-aminomethyl-4-(4-hydroxy-phenyl)-benzoic acid], [3-aminomethyl-4-(4-N,N-dimethyl-carboxamide-phenyl)-benzoic acid], [3-aminomethyl-4-(4-pyridyl)-benzoic acid], [3-aminomethyl-4-(4-quinolinyl)]-benzoic acid, [3-aminomethyl-4-(5-pyrimidinyl)-benzoic acid], [3-aminomethyl-4-(5-quinolinyl)-benzoic acid], [3-aminomethyl-4-(N,N-dimethyl)-benzoic acid], [3-aminomethyl-4-(piperonyl)-benzoic acid], [3-aminomethyl-4-[(2,3,4-tri-methoxy)-phenyl]-benzoic acid], [3-aminomethyl-4-[2-(1-piperazinyl)phenyl]-benzoic acid], [3-aminomethyl-4-[2-(3-(piperidin-4-ylmethoxy)phenyl]-benzoic acid], [3-aminomethyl-4-[3-(1-piperazinyl)-benzoic acid], [3-aminomethyl-4-[4-(1-piperazinyl)phenyl]-benzoic acid], [3-aminomethyl-4-[4-(1-piperazinyl)-phenyl]-benzoic acid], [3-aminomethyl-4-[4-(1-piperazinyl-4-AlexaFluor 647)phenyl]-benzoic acid], [3-aminomethyl-4-[4-(1-piperazinyl-4-FITC)phenyl]-benzoic acid], [3-aminomethyl-4-[5-(2,4-dimethyl)thiazole]-benzoic acid], [3-aminomethyl-5-(4-aza-phenyl)-benzoic acid], [4-(2,6-dimethyl-phenyl)-Phe], [4-(2-chloro-6-methoxy-phenyl)-Phe], [4-(2-methoxy-phenyl)-Phe], [4-(2-trifluoromethoxy-phenyl)-Phe], [N-methyl-3-aminomethyl-4-(4-quinolinyl)-benzoic acid], 1Nal, 2Igl, 2Nal, Aic, alphaMePhe, Atc, betaHomoLys, betahomoMet, BetaHomoPhe, Bip, Cha, Chg, cycloLeu, d2Igl, Dap(Cbz), dArg, dhomoPhe, dLys, dMet, dNle, dOrn, dOrn(dimethyl), dPip, dPro, dSer(OBn), dTic, dTiq, dTrp, dTyr, dTyr(OAllyl), dTyr(OBn), F, H, His(Bn), HomoPhe, Hyp, Hyp(OBn), Igl, K, M, MeMet, MePhe, metaY(Opr), MeTyr, Nva, Orn(acetamide), Orn (benzamide), Orn(ethylcarbamate), Orn(methanesulfonamide), Orn(pentyl amide), P, Phe-reduced, Pip, R, Tic, Tyr(2-methoxy diaryl ether), Tyr(2-tolyl diaryl ether), Tyr (3,4-difluoro diaryl ether), Tyr(3,4-dimethyl diaryl ether), Tyr(3-CO2Me diaryl ether), Tyr(3-fluoro diaryl ether), Tyr (3-methoxy diaryl ether), Tyr(3-methyl diaryl ether), Tyr(4-CF3 diaryl ether), Tyr(4-CO2H diaryl ether), Tyr(4-CO2Me diaryl ether), Tyr(4-fluoro diaryl ether), Tyr(4-methoxy diaryl ether), Tyr(OAllyl), Tyr(OPh), W, or Y.

In some embodiments, $X^z$ is dThr, P, dPro, Sar, cycloLeu, dLys, dArg, dSer, Pip, dTic, dPip, Hyp, dHyp, (cis-dHyp), dMeLys, dNle, dMeArg, G, A, dAla, dVal, dPro, Aze, betaHomoPro, 2Abz, betaHomoIle, dbetaHomoPro, betaHomoNle, MebetaHomoLys(Me)2, (3-aminomethyl-4-bromo-benzoic acid), [3-aminomethyl-4-(4-aza-phenyl)-benzoic acid], [3-aminomethyl-4-(2,5-dimethyl-isoxazole)-benzoic acid], or [3-aminomethyl-4-(3-aminomethyl-phenyl)-benzoic acid].

In some embodiments, $X^z$ is not betaHomoLys.

In some embodiments, $X^z$ is not a beta amino acid.

In some embodiments, the compound comprises a 21-membered ring.

In some embodiments, the compounds is any one of compounds 1-19.

In an aspect, there is provided a multimer comprising a plurality of the compounds described herein covalently linked together.

In some embodiments of the multimer, the plurality of compounds are all identical.

In some embodiments, the multimer is a dimer.

In some embodiments, the multimer is trimer.

In some embodiments, the multimer is a tetramer.

In some embodiments, the multimer is a pentamer.

In some embodiments of the multimer, the compounds are linked by a linker.

In some embodiments of the multimer, the compounds are linked together at the carbon associated with $R^4$, $R^5/R^6$ or $X^y$.

In an aspect, there is provided a pharmaceutical composition comprising the compound or multimer described herein along with the pharmaceutically acceptable carrier.

The term "pharmaceutically acceptable salt," as used herein, represents salts or zwitterionic forms of the compounds of the present invention which are water or oil-soluble or dispersible, which are suitable for treatment of diseases without undue toxicity, irritation, and allergic response; which are commensurate with a reasonable benefit/risk ratio, and which are effective for their intended use. The salts can be prepared during the final isolation and purification of the compounds or separately by treatment of an amino group with a suitable acid. Representative acid addition salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, fumarate, hydrochloride, hydrobromide, hydroiodide, 2-hydroxyethansulfonate (isethionate), lactate, maleate, mesitylenesulfonate, methanesulfonate, naphthylenesulfonate, nicotinate, 2-naphthalenesulfonate, oxalate, pamoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Also, amino groups in the compounds of the present invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. In certain embodiments, any of the peptide compounds described herein are salt forms, e.g., acetate salts.

As used herein, "pharmaceutically acceptable carrier" means any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the pharmacological agent.

In some embodiments, the pharmaceutical composition is formulated for oral delivery, topical delivery or parenteral delivery.

In an aspect, there is provided a method of treating inflammation or an autoimmune disease in a patient, comprising administering to the patient a therapeutically effective amount of the compound or multimer described herein.

In some embodiments, the inflammation or an autoimmune disease is gastrointestinal.

In an aspect, there is provided a method for treating a condition in a patient associated with a biological function of an α4β7 integrin, the method comprising administering to the patient a therapeutically effective amount of the compound or multimer described herein.

In some embodiments, the condition or disease is Inflammatory Bowel Disease (IBD), ulcerative colitis, Crohn's disease, Celiac disease (nontropical Sprue), enteropathy associated with seronegative arthropathies, microscopic colitis, collagenous colitis, eosinophilic gastroenteritis, colitis associated with radiotherapy or chemotherapy, pouchitis resulting after proctocolectomy and ileoanal anastomosis, gastrointestinal cancer, pancreatitis, insulin-dependent diabetes mellitus, mastitis, cholecystitis, cholangitis, pericholangitis, chronic bronchitis, chronic sinusitis, asthma, primary sclerosing cholangitis, human immunodeficiency virus (HIV) infection in the GI tract, eosinophilic asthma, eosinophilic esophagitis, gastritis, colitis, microscopic colitis, graft-versus-host disease, colitis associated with radio- or chemo-therapy, colitis associated with disorders of innate immunity as in leukocyte adhesion deficiency-1, chronic granulomatous disease, glycogen storage disease type Ib, Hermansky-Pudlak syndrome, Chediak-Higashi syndrome, Wiskott-Aldrich Syndrome, various forms of gastrointestinal cancer, osteoporosis, arthritis, multiple sclerosis, chronic pain, weight gain, or depression.

Preferably, the condition is an inflammatory bowel disease, further preferably, ulcerative colitis or Crohn's disease.

In an aspect, there is provided a method for treating a disease or condition in a patient comprising administering to the patient a therapeutically effective amount of the compound or multimer described herein, wherein the disease or condition is a local or systemic infection of a virus or retrovirus.

In some embodiments, the a virus or retrovirus is echovirus 1 and 8, echovirus 9/Barty Strain, human papilloma viruses, hantaviruses, rotaviruses, adenoviruses, foot and mouth disease virus, coxsackievirus A9, human parechovirus 1 or human immunodeficiency virus type 1.

In an aspect, there is provided a method for treating a disease or condition in a patient comprising administering to the patient a therapeutically effective amount of the compound or multimer described herein, wherein the disease or condition is hepatitis A, B or C, hepatic encephalopathy, non-alcoholic steatohepatitis, cirrhosis, variceal bleeding, hemochromatosis, Wilson disease, tyrosinemia, alpha-1-antitrypsin deficiency, hepatocellular carcinoma, liver cancer, primary biliary cholangitis, primary biliary sclerosis, biliary tract disease, or autoimmune hepatitis In some embodiments, the compound inhibits binding of α4β7 integrin to MAdCAM.

In some embodiments, the compound selectively inhibits binding of α4β7 integrin to MAdCAM.

In some embodiments, the patient is a human.

In other aspects, there is provided the use of the compounds or multimers described herein for treating or preventing the diseases and conditions noted above.

In other aspects, there is provided the use of the compounds or multimers described herein in the preparation of a medicament for treating or preventing the diseases and conditions noted above.

In other aspects, there is provided compounds or multimers described herein for use in treating or preventing the diseases and conditions noted above.

As used herein, the terms "disease", "disorder", and "condition" may be used interchangeably.

As used herein, "inhibition," "treatment," "treating," and "ameliorating" are used interchangeably and refer to, e.g., stasis of symptoms, prolongation of survival, partial or full amelioration of symptoms, and partial or full eradication of a condition, disease or disorder in a subject, e.g., a mammal.

As used herein, "prevent" or "prevention" includes (i) preventing or inhibiting the disease, injury, or condition from occurring in a subject, e.g., a mammal, in particular, when such subject is predisposed to the condition but has not yet been diagnosed as having it; or (ii) reducing the likelihood that the disease, injury, or condition will occur in the subject.

As used herein, "therapeutically effective amount" refers to an amount effective, at dosages and for a particular period of time necessary, to achieve the desired therapeutic result. A therapeutically effective amount of the pharmacological agent may vary according to factors such as the disease state, age, sex, and weight of the individual, and the ability of the pharmacological agent to elicit a desired response in the individual. A therapeutically effective amount is also one in which any toxic or detrimental effects of the pharmacological agent are outweighed by the therapeutically beneficial effects.

In some embodiments, the compound is administered by a form of administration selected from the group consisting of oral, intravenous, peritoneal, intradermal, subcutaneous, intramuscular, intrathecal, inhalation, vaporization, nebulization, sublingual, buccal, parenteral, rectal, vaginal, and topical.

In some embodiments, the compound is administered as an initial does followed by one or more subsequent doses and the minimum interval between any two doses is a period of less than 1 day, and wherein each of the doses comprises an effective amount of the compound.

In some embodiments, the effective amount of the compound is the amount sufficient to achieve at least one of the following selected from the group consisting of: a) about 50% or greater saturation of MAdCAM binding sites on α4β7 integrin molecules; b) about 50% or greater inhibition of α4β7 integrin expression on the cell surface; and c) about 50% or greater saturation of MAdCAM binding sites on α4β7 molecules and about 50% or greater inhibition of α4β7 integrin expression on the cell surface, wherein i) the saturation is maintained for a period consistent with a dosing frequency of no more than twice daily; ii) the inhibition is maintained for a period consistent with a dosing frequency of no more than twice daily; or iii) the saturation and the inhibition are each maintained for a period consistent with a dosing frequency of no more than twice daily.

In some embodiments, the compound is administered at an interval selected from the group consisting of around the clock, hourly, every four hours, once daily, twice daily, three times daily, four times daily, every other day, weekly, bi-weekly, and monthly.

It is contemplated that the above disclosure of embodiments also includes any and all combinations of the various embodiments. The advantages of the present invention are further illustrated by the following examples. The examples and their particular details set forth herein are presented for illustration only and should not be construed as a limitation on the claims of the present invention.

Examples

Methods and Materials
Synthesis General
The below example protocols were used to synthesize each of the compounds described herein. Scheme 1 depicts the general synthetic route to Compound 8.

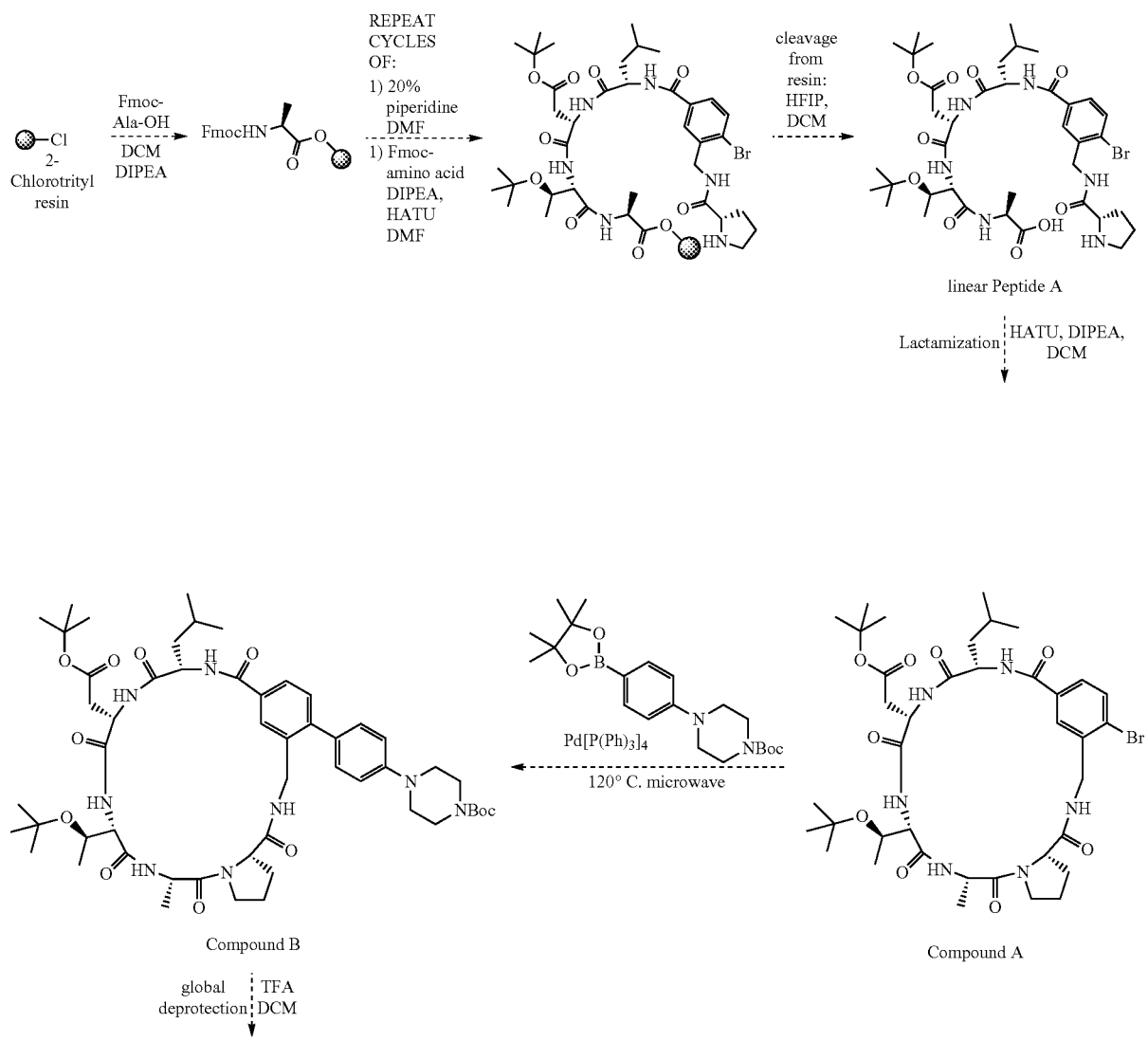

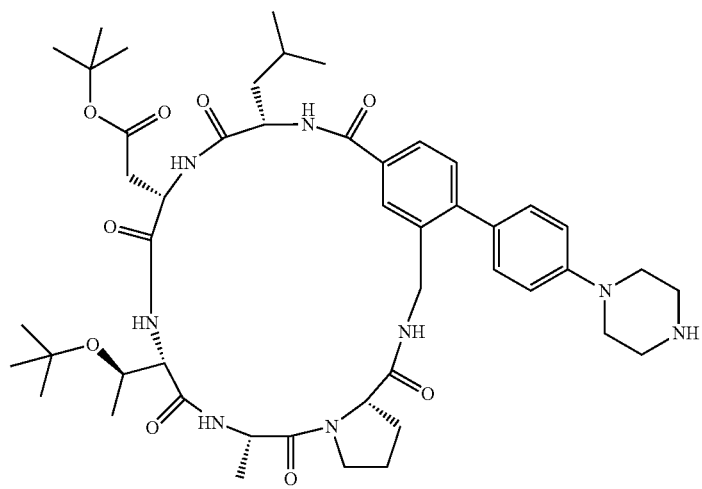

Compound 8

Synthesis of Resin-Bound Linear Peptide A

To a mixture containing 2-chlorotrityl resin (0.1 mmol, loading=1.0 mmol/g, 0.1 g) and Fmoc-Ala-OH (3 eq) was added DCM (10 mL), followed by DIEA (4.0 eq) in dropwise fashion. The resin was gently agitated for 1.5 hours. MeOH was added (0.1 mL) to end-cap any remaining reactive 2-chlorotrityl groups and the resin was gently agitated for 30 minutes and then drained.

The Fmoc-protected peptide resin was treated with 20% piperidine in DMF for 30 min. After removal of the Fmoc protecting group, the resin was drained and washed with DMF (5×5 mL). Standard Fmoc solid-phase peptide chemistry was employed to install Fmoc-Thr(tBu)-OH, Fmoc-Asp(OtBu)-OH and Fmoc-Leu-OH using Fmoc amino acid (3 eq), HATU (2.85 eq) and DIPEA (3 eq) in DMF (1 mL) for 1 hour. Coupling reactions were monitored by ninhydrin color reaction. The resin was treated with Fmoc-3-aminomethyl-4-bromobenzoic acid (1.5 eq; prepared according to PCT No. PCT/CA2016/000274), HATU (1.5 eq) and DIPEA (3 eq) in DMF (300 mL) for 1 hour. The Fmoc-protected peptide resin was treated with 20% piperidine in DMF for 30 min. After removal of the Fmoc protecting group, the resin was drained and washed with DMF (5×5 mL). Standard Fmoc solid-phase peptide chemistry was employed to install Fmoc-Pro-OH, using Fmoc amino acid (3 eq.), HATU (2.85 eq) and DIPEA (3 eq) in DMF (1 mL) for 1 hour. After coupling, the resin was washed with DMF (5×100 mL). The Fmoc-protected peptide resin was treated with 20% piperidine in DMF for 30 min. After removal of the Fmoc protecting group, the resin was drained and washed with DMF (5×5 mL). After the last step, the resin was washed with MeOH (3×100 mL), and dried under vacuum.

Cleavage of Linear Peptide A from Resin

The peptide resin (10 g) was treated with the cleavage cocktail (20% HFIP/80% DCM, 1 L) for 0.5 hour under gentle agitation. The cleavage cocktail was collected in a 3 L Erlenmeyer flask. The resin was again treated with the cleavage cocktail (20% HFIP/80% DCM, 1 L) for 0.5 hour under gentle agitation. The cleavage cocktail was collected in the same 3 L Erlenmeyer flask. The combined cleavage cocktail solution was concentrated under reduced pressure to deliver the crude linear Peptide A (4.5 g).

Cyclization

Crude linear Peptide A (4.5 g) was dissolved in DCM (5 L) and treated with DIEA (4 eq) and HATU (2 eq). The mixture was stirred for 0.5 hour at room temperature. Conversion of linear peptide was monitored by LCMS. The volatiles were concentrated under reduced pressure to deliver the crude, cyclic peptide, Compound A (5 g).

Suzuki Cross-Coupling

Five reactions were carried out in parallel. A mixture of crude Compound A (1 g 1.2 mmol), and 4-(4-Boc-piperazino) phenylboronic acid pinacol ester (931 mg, 2.4 mmol) were combined in a microwave reactor vessel and dissolved in a 1,2-dimethoxyethane (5.4 mL) and ethanol (1.2 mL) at room temperature. Water (1.2 mL) was added to the solution, followed by $Na_2CO_3$ (254 mg, 2.4 mmol). The reaction flask was flushed for 5 to 10 min with nitrogen gas and charged with $Pd(P(Ph)_3)_4$ (277 mg 0.24 mmol). The tube was sealed and heated at 120° C. for 10 min under microwave. LC-MS showed complete consumption of cyclic peptide and one main peak with the desired m/z. The reaction mixture was filtered over a celite pad to remove $Pd(P(Ph)_3)_4$. The celite pad was washed with THF and the solvents were removed under vacuum to give a pale yellow crude solid, Compound B Global De-Protection The crude, fully side-chain-protected Compound B was treated with 500 mL of cleavage buffer (TFA:DCM=1:1) and stirred for 1 hour, The volatiles were concentrated under reduced pressure to deliver fully-deprotected Compound 8 (7 g).

Purification

The crude Compound 8 was submitted to preparative reverse-phase HPLC (A: 0.075% TFA in H2O; B: ACN), generating a TFA salt of the purified cyclic peptide. A second preparative reverse-phase HPLC treatment (A: 1 mmol/L $NH_4HCO_3$ in $H_2O$; B: ACN) removed all traces of residual TFA and delivered Compound 8 as the "salt-free" form (800 mg) as a white solid, after lyophilization.

Dimerization of Compound 8: Synthesis of Compound 16
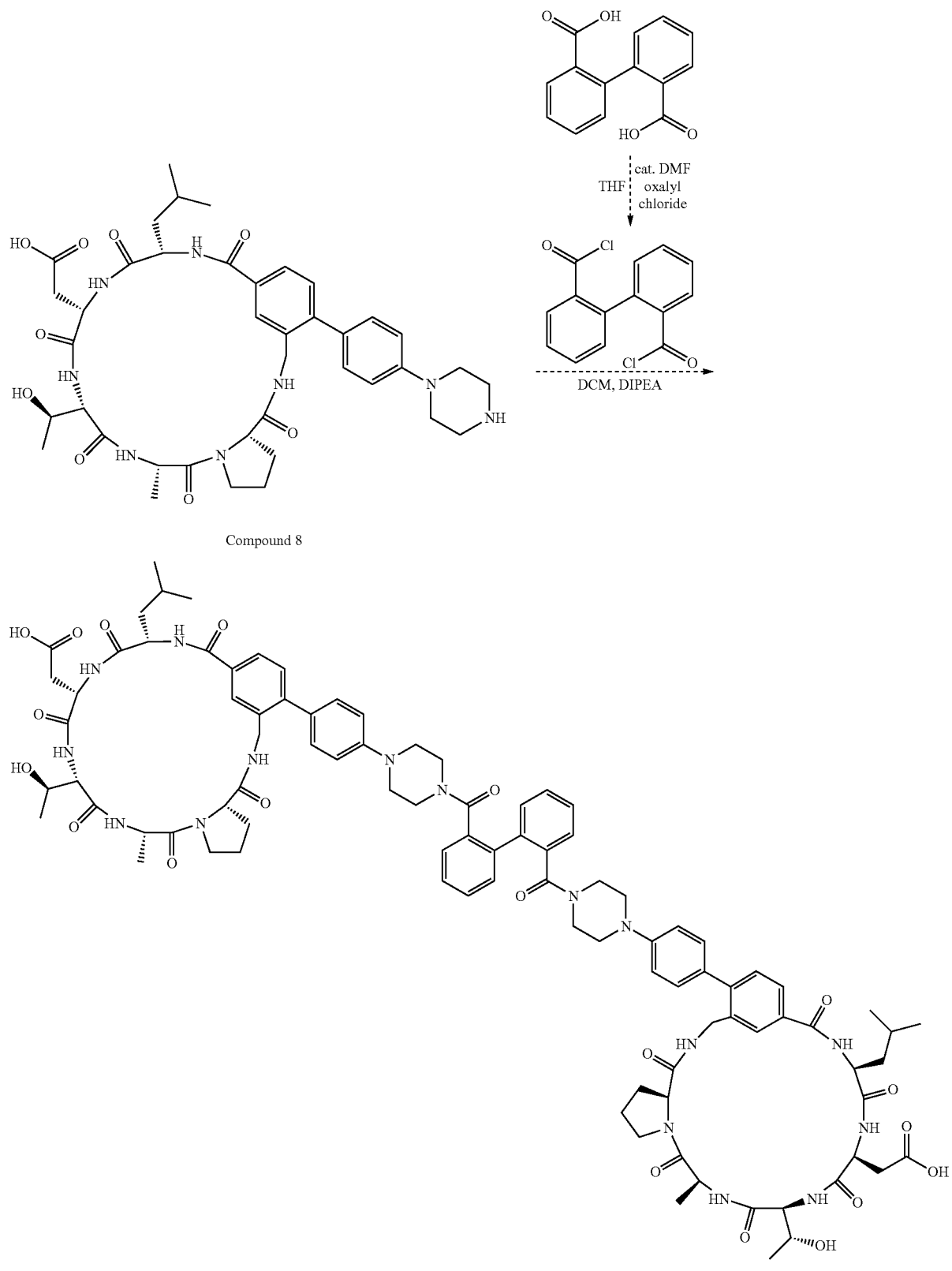

A solution of diphenic acid (12.1 mg, 0.05 mmol, 1.0 eq) in anhydrous THF (1 mL) was treated with oxalyl chloride (10 μl), followed by DMF (5 μl). The resulting suspension was stirred at 25° C. and became a yellow solution over the course of 1 hour. The volatiles were removed by flushing the flask with Argon. The resultant yellow solid was dissolved in anhydrous DCM (3 ml) and treated with Compound 8 (95 mg, 0.12 mmol, 2.4 eq; salt-free form). DIPEA (1.6 mL, 1.25 mmol, 25.0 Eq) was added dropwise to the mixture. The reaction was monitored by LC-MS. After 30 minutes, the volatiles were removed under vacuum and the crude material was purified by preparative reverse-phase HPLC (A: 0.075% TFA in H2O, B: ACN). Compound 16 was isolated as a white solid (9.4 mg).

Dimerization of Compound 8: Synthesis of Compound 18 stirred at 25° C. for 1 hour. The volatiles were removed under vacuum and the crude material was purified by preparative reverse-phase HPLC (A: 0.075% TFA in H2O, B: ACN). Compound 18 was isolated as a white solid (4.2 mg).

Integrin α4β7-MAdCAM-1 ELISA Competition Assay

A 96-well Microlon plate (Greiner, 655001) was coated with 100 μl per well of a solution of 1 μg/ml recombinant integrin α4β7 (R&D Systems, 5397-A3-050) in carbonate buffer (50 mM, pH 9.6). The plate was incubated at 4'C overnight. The solution was removed and 250 μl blocking buffer (50 mM Tris, 150 mM NaCl, 1 mM $MnCl_2$, 1% BSA, 0.05% Tween) was added per well. The plate was then incubated for 1 hour at room temperature. The plate was washed three times with wash buffer (50 mM Tris, 100 mM NaCl, 1 mM $MnCl_2$, 0.05% Tween). To each well, 50 μl of compound diluted in assay buffer was added by transfer from a compound serial dilution plate. 50 μl recombinant

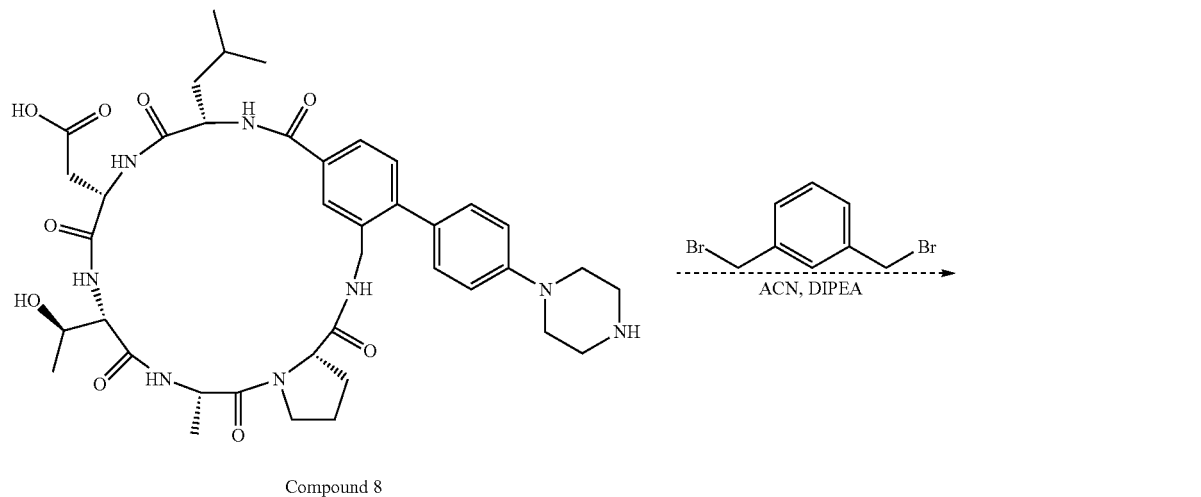

Compound 8

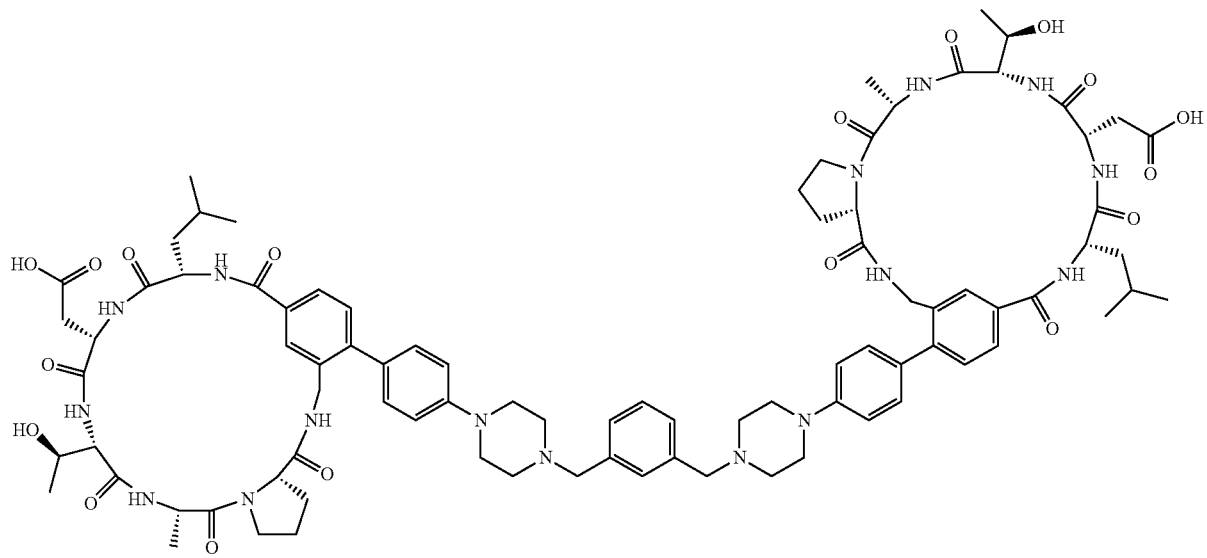

Compound 18

A suspension of Compound 8 (120 mg, 0.13 mmol, 2.7 eq; salt-free form), 1,3-bis(bromomethyl)benzene (12.8 mg, 0.05 mmol, 1 eq) and DIPEA (0.1 mL) in ACN (1 mL) was MAdCAM-Fc (R&D systems, 6056-MC-050) at a concentration of 0.1 µg/ml in assay buffer (50 mM Tris, 150 mM NaCl, 1 mM $MnCl_2$, 0.1% BSA, 0.05% Tween) was added to each well. The plate was incubated at room temperature with shaking (300 rpm) for 2 hours to reach binding equilibrium. Then the plate was washed three times in wash buffer and 100 µl anti-human IgG Fc specific-HRP (Abcam, Ab97225) diluted at 1:2000 in assay buffer was added to each well. The plate was incubated at room temperature for 1 hour under agitation. The plate was then washed three times and 100 µl of 1,3',5,5'-Tetramethylbenxidie (TMB, KPL 5120-0083) was then added to each well. The reaction was stopped after 2 minute-incubation by adding 50 µl of 1M $H_2SO_4$ and optical absorbance was read at 450 nM.

Integrin α4β1-VCAM-1 Competition ELISA

A 96-well Microlon plate (Greiner, 655001) was coated with 100 µl per well of a solution of 0.5 µg/ml recombinant integrin α4β1 (R&D Systems, 5397-A3-050) in carbonate buffer (50 mM, pH 9.6). The plate was incubated at 4° C. overnight. The solution was removed and 250 µl blocking buffer (50 mM Tris, 150 mM NaCl, 1 mM $MnCl_2$, 1% BSA, 0.05% Tween) was added per well. The plate was then incubated for 1 hour at room temperature. The plate was washed three times with wash buffer (50 mM Tris, 100 mM NaCl, 1 mM $MnCl_2$, 0.05% Tween). To each well, 50 µl of compound diluted in assay buffer was added by transfer from a compound serial dilution plate. 50 µl recombinant VCAM-Fc (R&D systems, 862-VC-100) at a concentration of 0.1 µg/ml in assay buffer (50 mM Tris, 150 mM NaCl, 1 mM $MnCl_2$, 0.1% BSA, 0.05% Tween) was added to each well. The plate was incubated at room temperature with shaking (300 rpm) for 2 hours to reach binding equilibrium. Then the plate was washed three times in wash buffer and 100 µl anti-human IgG Fc specific-HRP (Abcam, Ab97225) diluted at 1:2000 in assay buffer was added to each well. The plate was incubated at room temperature for 1 hour under agitation. The plate was then washed three times and 100 µl of 1,3',5,5'-Tetramethylbenxidie (TMB, (TMB, KPL 5120-0083) was then added to each well. The reaction was stopped after 2 minute-incubation by adding 50 µl of 1M $H_2SO_4$ and optical absorbance was read at 450 nM.

Integrin α4β7-MAdCAM Human Cell Adhesion Assay

RPM18866 human cells (Sigma #95041316) were cultured in RPMI 1640 medium (HyClone SH30027.1) supplemented with 10% FBS (Seradigm) and 1% Penicillin-Streptomycin. A 96-well plate (Costar, 3603) was coated with 100 µl/well of human recombinant human MAdCAM-1 Fc Chimera (R&D Systems, 6056-MC-050) solution at 0.25 µg/ml in coating buffer (50 mM sodium carbonate, pH 9.6). The plate was incubated overnight at 4° C. and washed twice with 150 µl per well wash buffer (0.05% Tween 20 in PBS), blocked with 250 µl per well blocking buffer (1% non-fat dry milk in PBS), and incubated for 2 hours at room temperature. RPM18866 cells were resuspended at 10 million cells/ml in PBS containing 5 mM calcein and incubated at 37° C. for 30 min in a 50 ml tube. PBS was added to fill the tube, cells were spun down and resuspended in RPMI 1640 medium to 2 million/ml. Compounds were diluted by serial dilution in binding buffer (1.5 mM $CaCl_2$ 0.5 mM $MnCl_2$, 50 mM Tris-HCl, pH 7.5) to a final volume of 50 µl per well at 2× concentration. The plate was washed once with 300 µl of PBS, 50 µl of compound and 50 µl of cells (100,000 cells) were transferred to each well and the plate was incubated in the dark at 37° C., 5% $CO_2$ for 45 min to allow cell adhesion. The plate was emptied by inverting and blotting on paper towels and washed manually twice with PBS. 100 µl PBS was then added to each well. The fluorescence was read ($Ex_{495}/Em_{515}$) using a plate reader (Tecan Infinite 1000). To calculate the dose response, the fluorescence value of control wells not containing cells was subtracted from each test well.

Integrin α4β1-VCAM Human Cell Adhesion Assay

RAMOS human cells (ATCC CRL-1596) were cultured in RPMI 1640 medium (HyClone SH30027.1) supplemented with 10% FBS (Seradigm) and 1% Penicillin-Streptomycin. A 96-well plate (Costar, 3603) was coated with 100 µl/well of recombinant human VCAM-1 Fc Chimera (R&D systems, 862-VC-100) solution at 0.25 µg/ml in coating buffer (50 mM sodium carbonate, pH 9.6). The plate was incubated overnight at 4° C. and washed twice with 150 µl per well wash buffer (0.05% Tween 20 in PBS), blocked with 250 µl per well blocking buffer (1% non-fat dry milk in PBS), for 1 hour at room temperature. During blocking step, RAMOS cells were resuspended at 10 million cells/ml in PBS containing 5 mM calcein and incubated at 37° C. for 30 min in a 50 ml tube. PBS was added to fill the tube, cells were spun down and resuspended in RPMI 1640 medium to 2 million/mi. Compounds were diluted by serial dilution in binding buffer (1.5 mM $CaCl_2$, 0.5 mM $MnCl_2$, 50 mM Tris-HCl, pH 7.5) to a final volume of 50 µl per well at 2× concentration. The plate was washed once with 300 µl of PBS, 50 µl of compound and 50 µl of cells (100,000 cells) were transferred to each well and the plate was incubated in the dark at 37° C., 5% $CO_2$ for 45 min to allow cell adhesion. The plate was emptied by inverting and blotting on paper towels and washed manually twice with PBS. After last wash, 100 µL of PBS was added to wells and the fluorescence was read ($Ex_{495}/Em_{515}$) using a plate reader (Tecan Infinite 1000). To calculate the dose response, the fluorescence value of control wells not containing cells was subtracted from each test well.

Integrin α4β7-MAdCAM Mouse Cell Adhesion Assay

TK-1 mouse T-cells lymphoma cell lines (ATCC CRL2396) were cultured in RPMI 1640 medium (HyClone SH30027.1) supplemented with 10% FBS (Seradigm) and 1% Penicillin-Streptomycin. A 96-well plate (Costar, 3603) was coated with 100 µl/well of recombinant mouse MAdCAM-1 Fc Chimera (R&D Systems, 993-MC-050) solution at 0.25 µg/ml in coating buffer (50 mM sodium carbonate, pH 9.6). The plate was incubated overnight at 4° C. and washed twice with 150 µl per well wash buffer (0.05% Tween 20 in PBS), blocked with 250 µl per well blocking buffer (1% non-fat dry milk in PBS), and incubated for 2 hours at room temperature. TK-1 cells were resuspended at 10 million cells/ml in PBS containing 5 mM calcein and incubated at 37° C. for 30 min in a 50 ml tube. PBS was added to fill the tube, cells were spun down and resuspended in RPMI 1640 medium to 2 million/ml. Compounds were diluted by serial dilution in binding buffer (1.5 mM $CaCl_2$, 0.5 mM $MnCl_2$, 50 mM Tris-HCl, pH 7.5) to a final volume of 50 µl per well at 2× concentration. The plate was washed once with 300 µl of PBS, 50 µl of compound and 50 µl of cells (100,000 cells) were transferred to each well and the plate was incubated in the dark at 37° C., 5% $CO_2$ for 45 min to allow cell adhesion. The plate was emptied by inverting and blotting on paper towels and washed manually twice with PBS. 100 µl PBS was then added to each well. The fluorescence was read ($Ex_{495}/Em_{515}$) using a plate reader (Tecan Infinite 1000). To calculate the dose response, the fluorescence value of control wells not containing cells was subtracted from each test well.

Analyte Competition Assay in Human CD4+ Integrin $\alpha_4+\beta_7$–Negative Memory Primary T Cells Receptor occupancy (RO) in primary cells was determined by measuring the amount of biotinylated human recombinant MAdCAM-1-FC or human recombinant VCAM-1-Fc bound to selected cell populations using flow cytometry. Human recombinant MAdCAM-1-FC or human recombinant VCAM-1-FC (R&D systems) were biotinylated using commercially available reagents and protocol (Pierce).

Whole blood was collected from human donors in sodium heparin tubes. A volume of 100 µL of blood was incubated with compound and 4 mM $MnCL_2$ for 1 hour at room temperature. Cells were washed twice with 1 mL of 1×DPBS calcium magnesium free(CMF) (ThermoFisher Scientific) and resuspended in 100 µL of DPBS CMF.

Biotinylated human recombinant MAdCAM-1-Fc or VCAM-1-Fc were added at saturating concentration and incubated at room temperature for 1 hour. A volume of 2 mL of 1×BD FACS Lyse (BD Biosciences) was then added and the mixture was incubated for 8-12 minutes at room temperature in the dark to lyse red blood cells. Cells were washed with 1 mL stain buffer-FBS (BD Biosciences) and resuspended in 100 µl stain Buffer-FBS (BD Biosciences) containing 4 mM $MnCl_2$. Biotinylated-rhMAdCAM-1 was applied at a saturating concentration of 1200 ng/mL to compete with test article binding and incubated at room temperature for 1 hour. Cells were then washed with 1 mL stain buffer-FBS and resuspended in 100 µl stain buffer-FBS. The cells were incubated in the dark for 30 minutes at room temperature with 1 µl Streptavidin APC (Biolegend 0.2 mg/ml) and a panel of antibodies for the detection of memory T helper a4b7-positive cells subset. And amount of 5.0 µl each of the following antibodies were used; CD45 FITC (BioLegend 200 µg/ml), CD29 APC Cy7 (BioLegend 100 µg/ml), Integrin beta7 PE, (BioLegend concentration 50 µg/mL), CD49d V421 (BioLegend 50 µg/mL), CD3 V510 (BioLegend 30 µg/mL), CD4 PECy7 (BioLegend 100 µg/mL), CD45RO PerCP, BioLegend 200 µg/mL). The cells were then washed with stain-buffer-FBS and resuspended in 150 µL stain buffer-FBS for acquisition on the flow cytometer (BD FACSCanto™ flow cytometer and BDFACS-Diva™ software). FACS data was acquire by electronic gating on the basis of forward versus side scatter, The cytometer was set to collect 20,000 events in each tube. Cell population were determined using the following markers, CD45+, CD3+, CD4+, CD45RO+, CD49d+, integrin β7, biotinylated ligands.

Compound RO was defined as the decrease in the number of integrin $\beta_7$+ or integrin $\beta_7$–lo cells binding biotinylated rhMAdCAM-1 or rhVCAM-1, respectively.

Receptor occupancy was calculated with the following equation: 100−((% ligand-positive cells with compound/% ligand-positive cells DMSO)*100). Ligands and compounds did not compete for anti-integrin antibodies and interfere with the detection of the c$\alpha$4β7 positive memory T cells.

Results and Discussion

Compounds represented in FIGS. 1-5 were synthesized in accordance with the above-noted methods. A selection of compounds was characterized using HPLC, mass spectrometry and NMR (data not shown). In some instances, compounds isolated from a first-generation synthesis and purification (Batch 1) produced multiple peaks in the HPLC chromatogram. In some of those instances, a second- and/or third-generation synthesis and purification was undertaken, resulting in Batch 2 and/or Batch 3 materials that exhibited essentially single-peaks in the HPLC chromatograms. Batch 1, Batch 2 and Batch 3 designations were noted in HPLC, mass spectrometry and NMR data (not shown).

Competition Assays

Results of the compounds in two ligand competition assays (MAdCAM-1/α4β7 and VCAM-1/α4β1) are shown in Table 1.

Cell Adhesion Competition Assays

Results of the compounds in the RPM18866, RAMOS and TK-1 cell adhesion competition assays are shown in Tables 1, and 2.

Receptor Occupancy

Results of the compounds in the whole blood ligand displacement assays are shown in Tables 1 and 3

Binding Affinity and Selectivity of Compounds for Integrin α4β7 and α4β1

We measured binding potency for monomeric and dimeric compounds to α4β7-integrin using a battery of biochemical, cell-based and ex vivo assays. Multimeric compounds were generally more potent in biochemical and cellular assays, versus their constituent monomers.

Figure 6:
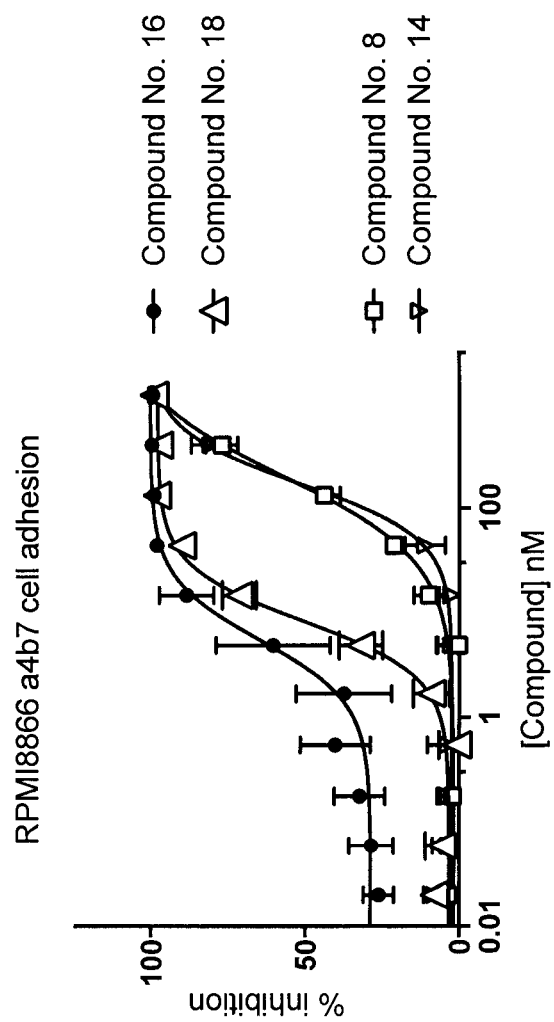
FIG. 6 shows the ability of the compounds to inhibit the adhesion of human cell lines expressing integrin α4β7 on plates coated with MAdCAM-1. Dose response curves for inhibition of RPM18866 cells expressing integrin α4β7 adhesion to MAdCAM-1 coated plates. Error bars indicate standard deviations.
Figure 7:
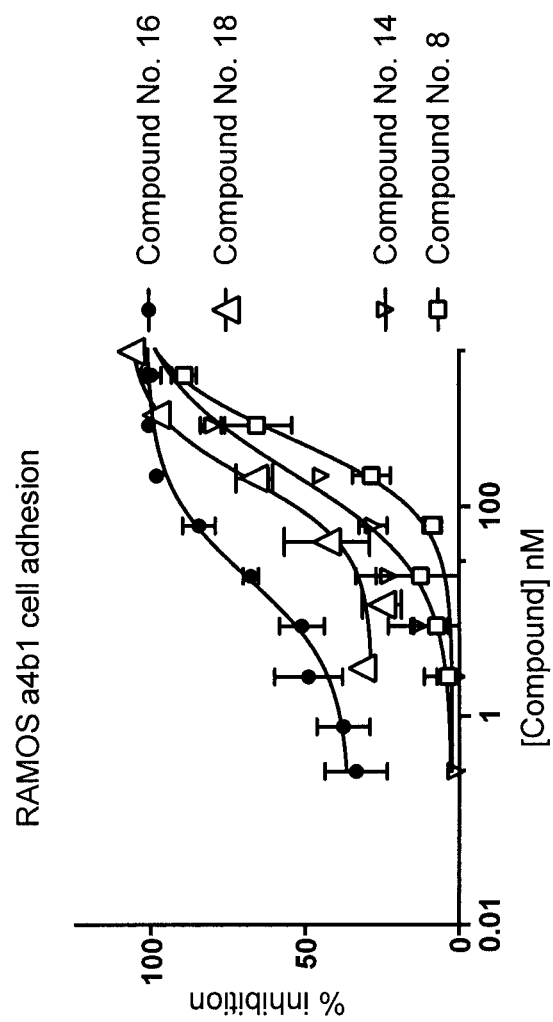
FIG. 7 shows the ability of the compounds to inhibit the adhesion of human cell lines expressing integrin α4β1 on plates coated with VCAM-1. Dose response curves for inhibition of RAMOS cells expressing integrin α4β1 adhesion to VCAM-1 coated plates. Error bars indicate standard deviations.

We measured the ability of test articles to prevent the adhesion of RPM18866 cells, which express human integrin α4β7, to plates coated with MAdCAM-1. Multimeric compounds were generally more potent in their ability to inhibit cell adhesion than their constituent monomers. For example, Compound No. 16 and Compound No. 8 had $IC_{50}$ values of ~6 nM and ~202 nM, respectively, in comparable RPMI8866 cell adhesion assays (FIG. 6; Tables 1 and 2). Multimeric compounds were generally also more selective than their constituent monomers in their ability to inhibit adhesion for cells expressing integrin α4β7 (RPMI8866) versus for cells expressing human integrin α4β1 (RAMOS; FIG. 7; Tables 1 and 2). For example, multimeric Compound No. 16 inhibited adhesion in RPMI8866 cells with an $IC_{50}$ value of ~6 nM and inhibited adhesion in RAMOS cells with an $IC_{50}$ value of ~21 nM (a 3.5-fold difference between the assays, in favor of integrin α4β7), whereas monomeric Compound No. 8 inhibited adhesion in RPM18866 cells with an $IC_{50}$ value of ~202 nM and inhibited adhesion in RAMOS cells with an $IC_{50}$ value of ~451 nM (a 2.2-fold difference between the assays, in favor of integrin α4β7). Taken together, multimerization of a monomer led to increased inhibition of cell adhesion, as well as increased selectivity in inhibition of cell adhesion, favoring integrin α4β7 versus integrin α4β1.

Interestingly, differences in binding affinity between monomeric and multimeric compounds were not as pronounced in the ELISA α4β7 binding assay. For example, monomeric Compound No. 8 exhibited an ELISA α4β7 $IC_{50}$ of ~24 nM, whereas dimeric Compound No. 16 exhibited an ELISA α4β7 $IC_{50}$ value of ~8 nM (Table 1). It is possible that avidity enhances the binding potency of multimeric compounds in cells.

Figure 8:
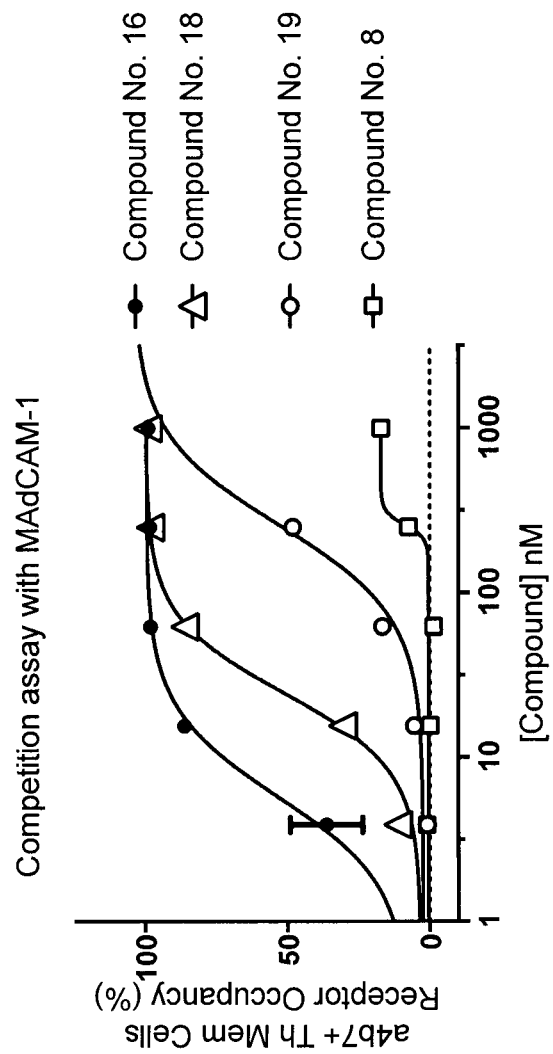
FIG. 8 shows compound receptor occupancy (RO), measured using a whole blood ligand displacement assay. Dose response curves for Inhibition of MAdCAM binding to α4β7 Th memory cells in a representative experiment. Error bars indicate standard deviation for duplicate data points for Compound No. 16.

Similar results were obtained in a ligand competition assay for binding to integrin α4β7 in human whole blood (Tables 1 and 3). Receptor occupancy of compounds was determined by measuring the proportion of α4β7+ memory T helper cells able to bind biotinylated rhMAdCAM-1 using flow cytometry. Multimeric compounds were able to compete with MAdCAM-1 on α4β7-positive primary cells with greater potency than monomeric compounds. Multimers containing a variety of linkers were shown to compete more effectively than their constituent monomer. For example, Dimeric Compound Nos. 16, 18 and 19 exhibited $IC_{50}$ values of ~6, 25 and ~260 nM, while for the corresponding parent monomeric Compound No. 8, a relatively weak concentration-response curve was obtained (FIG. 8; Table 3). This could be the result of non-specific binding of the monomeric compound to the cell.

Figure 9:
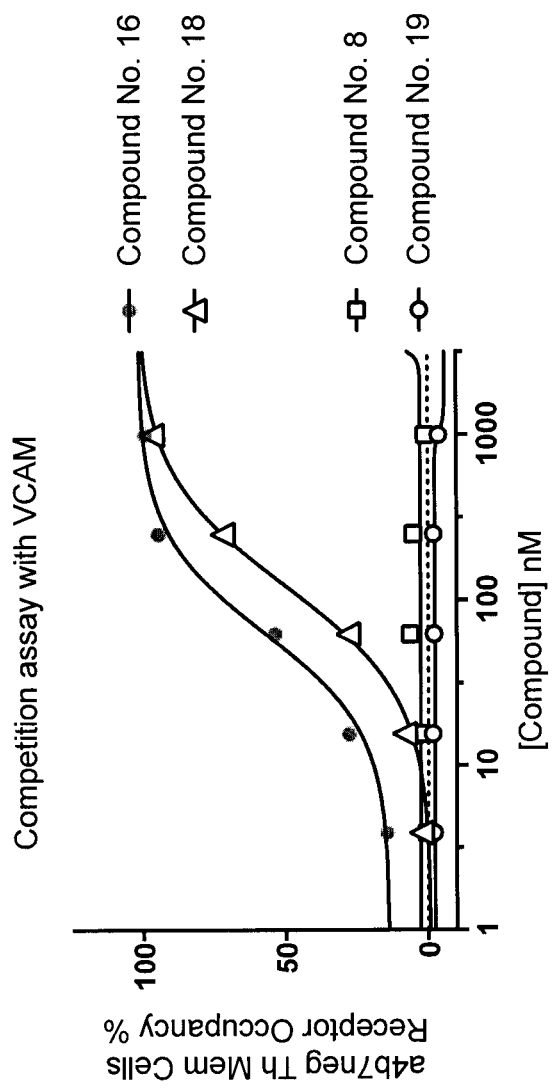
FIG. 9 shows compound receptor occupancy (RO), measured using a whole blood ligand displacement assay. Dose response curves for Inhibition of MAdCAM binding to α4β7-negative Th memory cells in a representative experiment.

Receptor occupancy, as measured by the analyte competition assay in human CD4+ integrin $\alpha_4+\beta_7$–lo memory primary T cells, identified multimeric compounds with considerable potency and selectivity favoring $\alpha 4\beta 7$ over $\alpha 4\beta 1$, in whole blood. Monomeric Compound No. 8 exhibited relatively weak RO at $\alpha 4\beta 7$ ($IC_{50}$>4 μM) (FIG. 8; Tables 1 and 3) and no selectivity versus $\alpha 4\beta 1$. Similar profiles were recorded for monomeric Compound Nos. 11 and 14. In contrast, multimer Compound No. 16, in particular, exhibited strong c$\alpha 4\beta 7$ RO ($IC_{50}$~6 nM) and strong (~11-fold difference in $IC_{50}$ between assays) selectivity versus $\alpha 4\beta 1$ (FIG. 9; Tables 1 and 3). Multimer Compound Nos. 18 and 19 also exhibited sub-micromolar $\alpha 4\beta 7$ RO $IC_{50}$ values, as well as selectivity versus $\alpha 4\beta 1$.

To assess adhesion in mouse cells, for comparison with human cells, we employed the murine TK-1 cell line, which expresses mouse integrin $\alpha 4\beta 7$ (Table 1). Monomeric Compound No. 8 exhibited ~10-fold difference in $IC_{50}$ between mouse $\alpha 4\beta 7$-containing cell adhesion (weaker adhesion) and human $\alpha 4\beta 7$-containing cell adhesion (stronger adhesion). Multimeric compounds generally exhibited lower discrepancies between mouse and human cell adhesion, versus monomer Compound No. 8. For example, multimeric Compound Nos. 16, 17 and 18 exhibited ~28, ~97 and ~68 nM $IC_{50}$ values in mouse $\alpha 4\beta 7$-containing cell adhesion, but ~6, ~19 and ~8 nM $IC_{50}$ values in human $\alpha 4\beta 7$-containing cell adhesion. One exception is multimer Compound No. 19, which exhibited an $IC_{50}$ value of 1.883 μM in mouse $\alpha 4\beta 7$-containing cell adhesion but an $IC_{50}$ value of ~25 nM in human $\alpha 4\beta 7$-containing cell adhesion.

Although preferred embodiments of the invention have been described herein, it will be understood by those skilled in the art that variations may be made thereto without departing from the spirit of the invention or the scope of the appended claims. All documents disclosed herein, including those in the following reference list, are incorporated by reference.

TABLE 1 shows homodetic compounds exhibiting α4β7 integrin affinity, selectivity and/or activity.

| Compound No. | α4β7 ELISA $IC_{50}$ (∝M)[a] | α4β1 ELISA $IC_{50}$ (∝M)[b] | human α4β7 cell adhesion RPMI 8866 $IC_{50}$ (∝M)[c] | human α4β1 cell adhesion Ramos $IC_{50}$ (∝M) | mouse α4β7 cell adhesion TK-1 $IC_{50}$ (∝M) | Whole Blood Ligand Displacement: inhibition of biotinylated hrMAdCAM-1 binding to α4β7+ Th mem cells ($IC_{50}$ in ∝M) | Whole Blood Ligand Displacement: inhibition of biotinylated hrVCAM-1 binding to α4β7-neg. Th mem cells ($IC_{50}$ in ∝M) |
|---|---|---|---|---|---|---|---|
| 1 | 9.391 | | | | | | |
| 2 | 35.00 | | | | | | |
| 3 | 1.378 | 1.666 | | | | | |
| 4 | 2.001 | 2.327 | | | | | |
| 5 | 5.811 | 4.798 | | | | | |
| 6 | 15.81 | 9.000 | | | | | |
| 7 | 0.030 | 0.007 | 0.201 | | | | |
| 8 | 0.035 | 0.010 | 0.125 | | | | |
| 8 | | | 0.260 | | | | |
| 8 | | | 0.125 | 0.451 | 1.331 | >4.0 | >4.0 |
| 8 | 0.024[d] | | 0.202[f] | | | | |
| 9 | 9.210 | 96.78 | | | | | |
| 10 | 9.358 | 55.55 | | | | | |
| 11 | 0.011 | 0.009 | 0.626 | 0.606 | | >1.0 | >4.0 |
| 12 | 0.020 | 0.031 | 0.672 | | | | |
| 13 | 0.038 | 0.013 | 0.307 | | | | |
| 14 | 0.007 | 0.009 | 0.231 | 0.217 | | >1.0 | >4.0 |
| 14 | | | 0.172[f] | | | | |
| 15 | 0.431 | 7.439 | 47.00 | | | | |
| 16 | | | 0.014 | | | | |
| 16 | | | 0.002 | 0.021 | 0.028 | 0.006 | 0.064 |
| 16 | | | 0.006[f] | | | | |
| 16 | 0.008[d] | 0.001[e] | | | | | |
| 17 | | | 0.007 | | | | |
| 17 | | | 0.004 | 0.166 | 0.097 | | 1.664 |
| 17 | | | 0.019[f] | | | | |
| 17 | 0.005[d] | 0.001[e] | | | | | |
| 18 | | | 0.042 | | | | |
| 18 | | | 0.002 | 0.184 | 0.068 | 0.025 | 0.123 |
| 18 | | | 0.008[f] | | | | |
| 19 | | | 0.060 | | | | |
| 19 | | | 0.025 | 0.080 | 1.883 | 0.260 | >4.0 |

[a]All α4β7 ELISA $IC_{50}$ values determined in a first run unless otherwise noted
[b]All α4β1 ELISA $IC_{50}$ values determined in a first run unless otherwise noted
[c]All human α4β7 cell adhesion RPMI8866 $IC_{50}$ values determined in a first run unless otherwise noted
[d]α4β7 ELISA $IC_{50}$ values determined in a second run
[e]α4β1 ELISA $IC_{50}$ values determined in a second run
[f]Human α4β7 cell adhesion RPMI8866 $IC_{50}$ values determined in a second run

TABLE 2

Homodetic compounds that inhibit adhesion of human
cell lines expressing integrin α4β7 on plates
coated with MAdCAM-1 (RPMI8866 cells) and integrin
α4β1 on plates coated with VCAM-1 (RAMOS cells).

| Compound No. | 16 | 18 | 8 | 14 |
|---|---|---|---|---|
| RPMI8866 IC$_{50}$ (nM) | 5.5 | 8.4 | 202 | 172 |
| RAMOS IC$_{50}$ (nM) | 21 | 184 | 451 | 217 |

TABLE 3

Homodetic compound receptor occupancy (RO), expressed
as inhibition of MAdCAM binding to a4b7 Th memory cells
(MAdCAM-1 competition IC$_{50}$), or to a4b7-negative Th memory
cells (VCAM competition IC$_{50}$).

| Compound No. | 16 | 18 | 19 | 8 |
|---|---|---|---|---|
| MAdCAM-1 Competition IC$_{50}$ (nM) | 5.807 | 24.73 | 259.7 | >4000 |
| VCAM Competition IC$_{50}$ (nM) | 63.76 | 123.2 | >4000 | >4000 |

The invention claimed is:

1. A dimer comprising two compounds of formula (I) covalently linked together, or a pharmaceutically acceptable salt thereof, wherein the compound of formula (I) has the structure:

wherein

R$^1$ is H; lower alkyl; aryl; heteroaryl; alkenyl; or heterocycle; all of which are optionally substituted with one or more substituents selected from the group consisting of H; hydroxyl; cyano; alkyl; alkoxy; aryloxy; vinyl; alkenyl; alkynyl; formyl; haloalkyl; halide; aryl; heteroaryl; amide; acyl; ester; ethers and thioethers; thioalkoxy; phosphino; and —NR$_a$R$_b$, where R$_a$ and R$_b$ are independently selected from lower alkyl, aryl or benzyl;

R$^2$ and R$^3$ are each independently an amino acid side chain of a proteinogenic or a non-proteinogenic alpha-amino acid, provided that R$^2$ and R$^3$ may be covalently linked to each other to form a ring or may be covalently linked to R$^1$ to form a cyclic secondary amine,

R$^4$ along with R$^5$ or R$^6$ forms a ring resulting in a proline residue having N—R$^4$ as its N-terminus;

R$^5$ and R$^6$ are independently selected from the amino acid side chains of a proteinogenic or a non-proteinogenic alpha-amino acid having the N-terminus thereof being the N—R$^4$, or may form a cyclic side chain with R$^4$;

stereocenters 1* and 2* are each independently selected from R and S; and wherein Z is an amino terminus of an amino acid; —C═O— adjacent L is the carboxy terminus of an amino acid; and L along with Z and —C═O— is a peptide having the following formula:

X$^y$—X$^z$—X$^1$—X$^2$—X$^3$ wherein X$^y$ is a moiety comprising a radical of 3-aminomethyl-benzoic acid;

X$^z$ is absent;

X$^1$ is Leucine or tert-butyl-Ala;

X$^2$ is Asp; and

X$^3$ is Thr, Ile, MeThr, alloThr, Abu, Thr(OBn), Val, or alloIle, wherein the two compounds of formula (I) are linked together at a carbon associated with X$^y$.

2. The dimer of claim 1, wherein R$^1$ is H.

3. The dimer of claim 1, wherein R$^2$ or R$^3$ is covalently linked to R to form proline having NR$^1$ as the N-terminus.

4. The dimer of claim 1, wherein R$^2$ and R$^3$ are not both H.

5. The dimer of claim 1, wherein R$^2$ and R$^3$ are H and CH$_3$ respectively or vice versa.

6. The dimer of claim 1, wherein R$^4$ and R$^6$ form a ring resulting in a proline residue having N—R$^4$ as its N-terminus.

7. The dimer of claim 1, wherein X$^1$ is Leu.

8. The dimer of claim 1, wherein X$^3$ is selected from the group consisting of Thr, Val, and Ile.

9. The dimer of claim 1, wherein X$^y$ comprises a radical of (3-aminomethyl-4-bromo-benzoic acid), (3-aminomethyl-4-morpholinyl-benzoic acid), (3-aminomethyl-4-piperidinyl-benzoic acid), (3-aminomethyl-5-bromo-benzoic acid), (3-aminomethyl-6-bromo-benzoic acid), (3-aminomethyl-benzoic acid), [3-aminomethyl-(4-methylpyrazole-3-yl)-benzoic acid], [3-aminomethyl-4-(2,5-dimethoxy-phenyl)-benzoic acid], [3-aminomethyl-4-(2,5-dimethyl-isoxazole)-benzoic acid], [3-aminomethyl-4-(2-aminomethylphenyl)-benzoic acid], [3-aminomethyl-4-(2-fluoro-pyridyl)-benzoic acid], [3-aminomethyl-4-(3-aminomethylphenyl)-benzoic acid], [3-aminomethyl-4-(3-aza-phenyl)-benzoic acid], [3-aminomethyl-4-(3-CF3-phenyl)-benzoic acid], [3-aminomethyl-4-(3-N,N-dimethylaniline)-benzoic acid], [3-aminomethyl-4-(3-N,N-dimethyl-diaryl ether)-benzoic acid], [3-aminomethyl-4-(3-quinolinyl)-benzoic acid], [3-aminomethyl-4-(3-thiophenyl)-benzoic acid], [3-aminoethyl-4-(4-aminomethylphenyl)-benzoic acid], [3-aminomethyl-4-(4-aza-phenyl)-benzoic acid], [3-aminomethyl-4-(4-carboxy)-phenyl)-benzoic acid], [3-aminomethyl-4-(4-hydroxy-phenyl)-benzoic acid], [3-aminomethyl-4-(4-N,N-dimethyl-carboxamide-phenyl)-benzoic acid], [3-aminomethyl-4-(4-pyridyl)-benzoic acid], [3-aminomethyl-4-(4-quinolinyl)]-benzoic acid, [3-aminomethyl-4-(5-pyrimidinyl)-benzoic acid], [3-aminomethyl-4-(5-quinolinyl)-benzoic acid], [3-aminomethyl-4-(N,N-dimethyl)-benzoic acid], [3-aminomethyl-4-(piperonyl)-benzoic acid], [3-aminomethyl-4-[(2,3,4-tri-methoxy)-phenyl]-benzoic acid], [3-aminomethyl-4-[2-(1-piperazinyl)phenyl]-benzoic acid], [3-aminomethyl-4-[2-(3-(piperidin-4-ylmethoxy)phenyl]- benzoic acid], [3-aminomethyl-4-[3-(1-piperazinyl)phenyl]-benzoic acid], [3-aminomethyl-4-[4-(1-piperazinyl)phenyl]-benzoic acid], [3-aminomethyl-4-[4-(1-piperazinyl)-phenyl]-benzoic acid], [3-aminomethyl-4-[4-(1-piperazinyl-4-AlexaFluor 647)phenyl]-benzoic acid], [3-aminomethyl-4-[4-(1-piperazinyl-4-FITC)phenyl]-benzoic acid], [3-aminomethyl-4-[5-(2,4-dimethyl)thiazole]-benzoic acid], and [3-aminomethyl-5-(4-aza-phenyl)-benzoic acid].

10. The dimer of claim 1, wherein the compound comprises a 21-membered ring.

11. The dimer of claim 1, being any one of the following compounds:

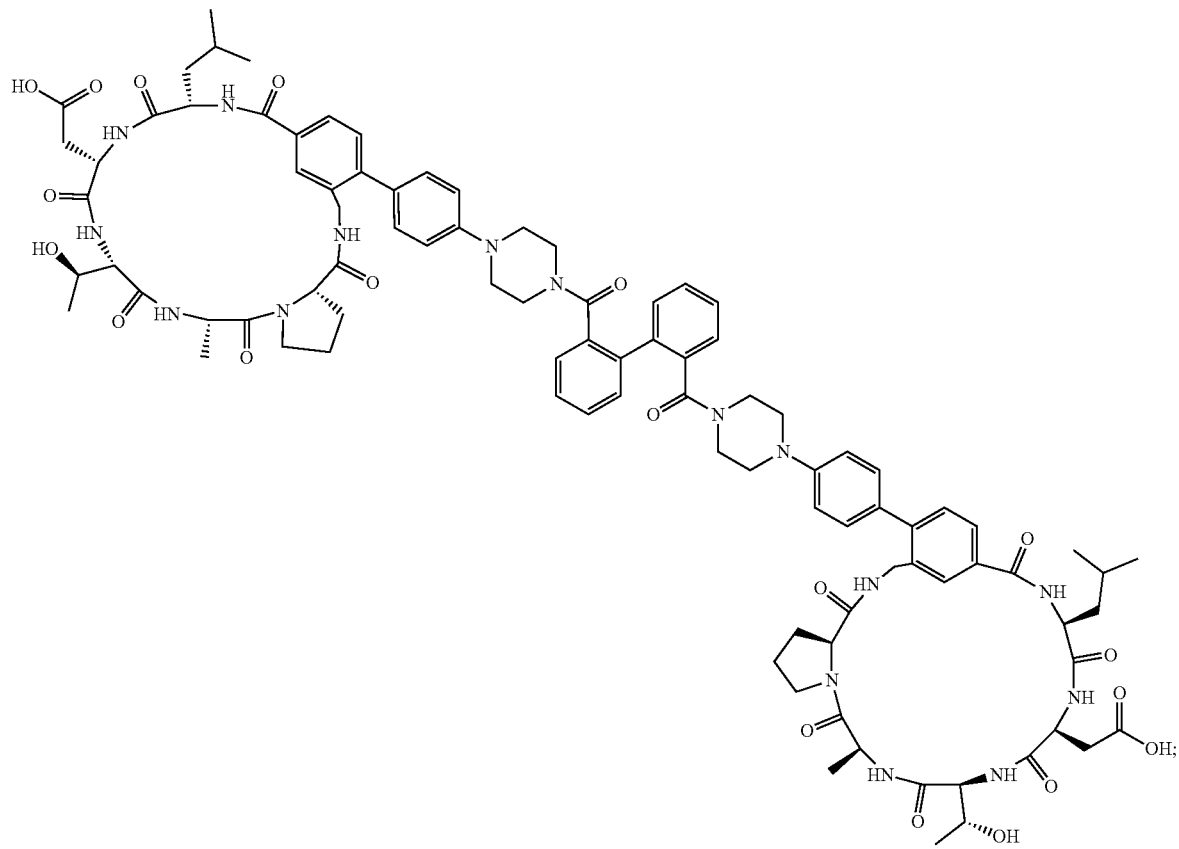

Compound 16

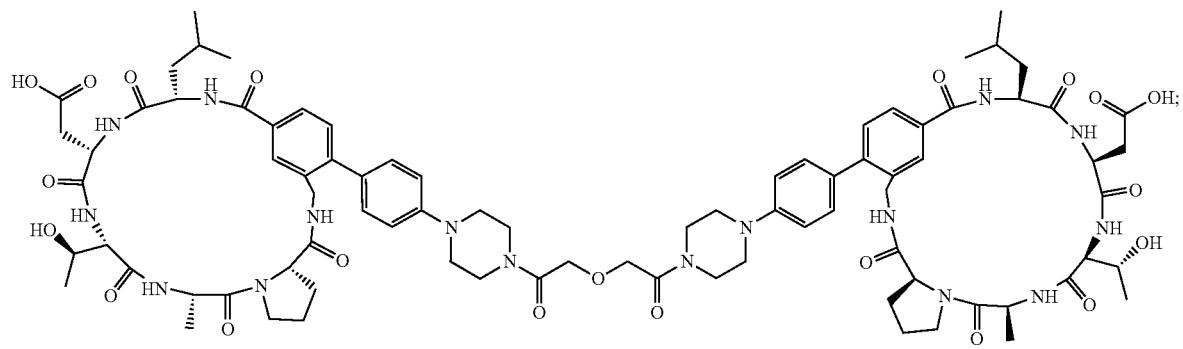

Compound 17

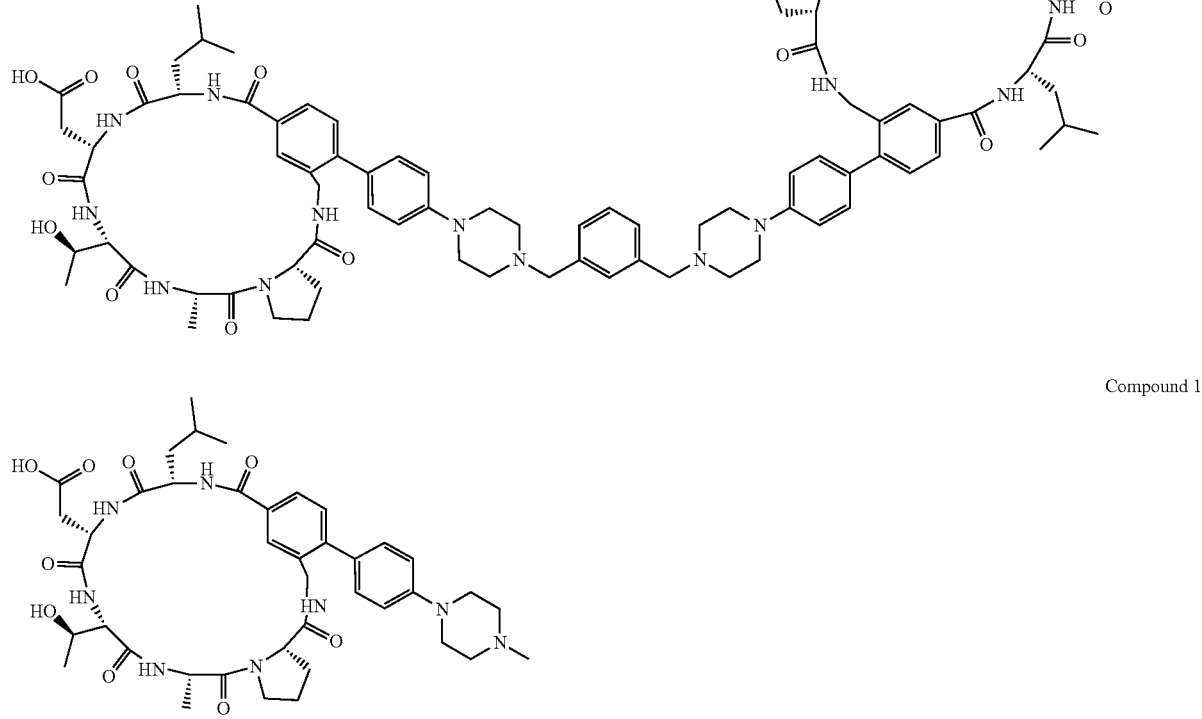

Compound 19

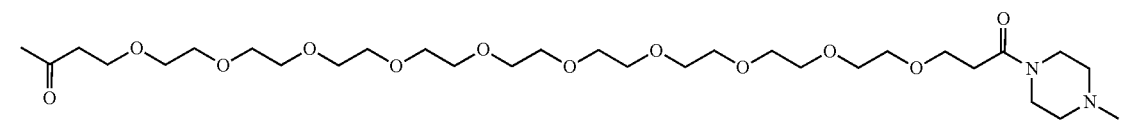

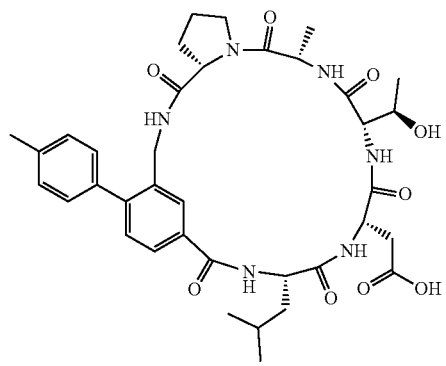

or a pharmaceutically acceptable salt thereof.

12. The dimer of claim 1, wherein the two compounds are identical.

13. A pharmaceutical composition comprising the dimer of claim 1 along with a pharmaceutically acceptable carrier.

14. A method of treating inflammation or an autoimmune disease in a patient, comprising administering to the patient a therapeutically effective amount of the dimer of claim 1.

15. The method of claim 14, wherein the condition or disease is selected from the group consisting of Inflammatory Bowel Disease (IBD); ulcerative colitis; Crohn's disease; Celiac disease; nontropical Sprue; enteropathy; pouchitis; gastrointestinal cancer; pancreatitis; insulin-dependent diabetes mellitus; mastitis; cholecystitis; cholangitis; pericholangitis; chronic bronchitis; chronic sinusitis; asthma; primary sclerosing cholangitis; human immunodeficiency virus (HIV) infection; eosinophilic asthma; eosinophilic esophagitis; gastritis; colitis; microscopic colitis; graft-versus-host disease; osteoporosis; arthritis; multiple sclerosis and chronic pain.

16. A method for treating a disease or condition in a patient comprising administering to the patient a therapeutically effective amount of the dimer of claim 1, wherein the disease or condition is a local or systemic infection of a virus or retrovirus.

17. A method for treating a disease or condition in a patient comprising administering to the patient a therapeutically effective amount of the dimer of claim 1, wherein the disease or condition is selected from the group consisting of hepatitis A, B or C, hepatic encephalopathy, non-alcoholic steatohepatitis, cirrhosis, variceal bleeding, hemochromatosis, Wilson disease, tyrosinemia, alpha-1-antitrypsin deficiency, hepatocellular carcinoma, liver cancer, primary biliary cholangitis, primary biliary sclerosis, biliary tract disease, and autoimmune hepatitis.

18. The dimer of claim 1, wherein the dimer is:

Compound 16

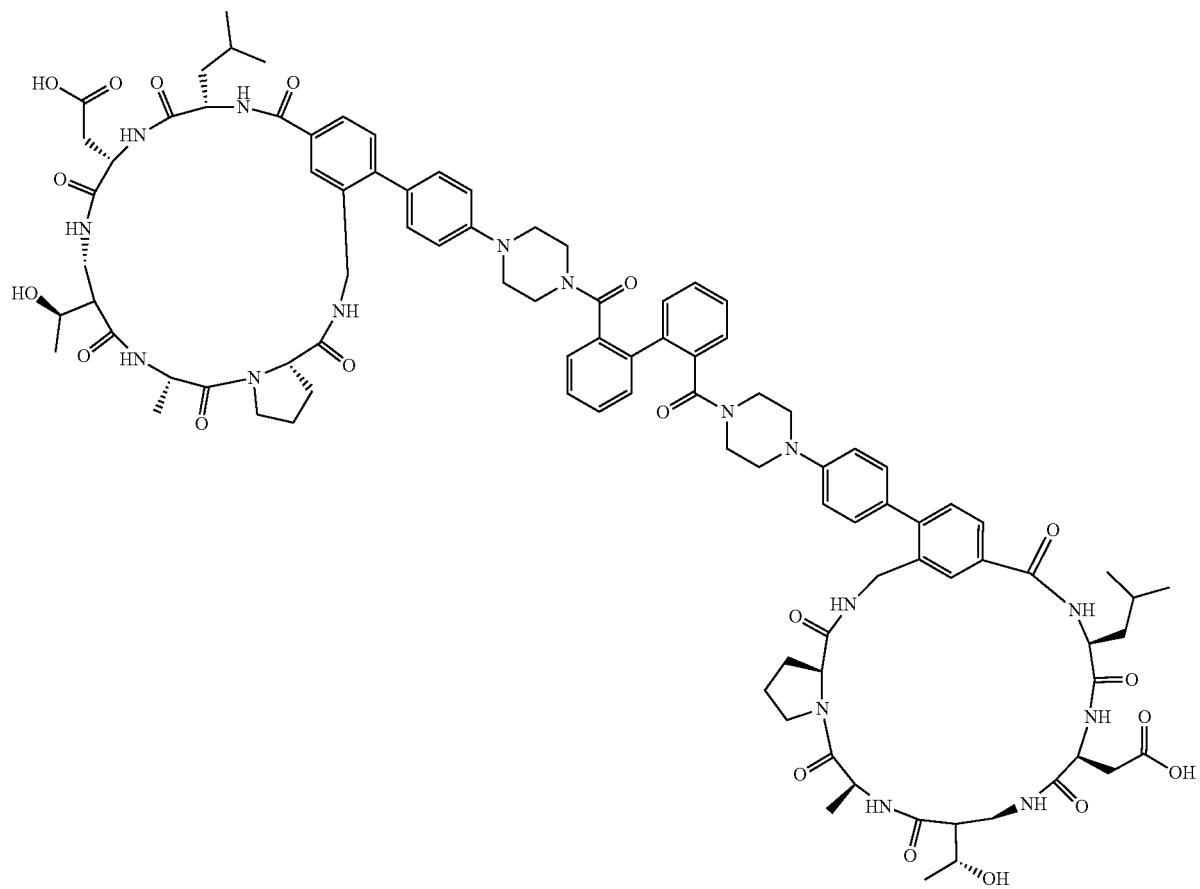

or a pharmaceutically acceptable salt thereof.

* * * * *